(12) United States Patent
Väyrynen et al.

(10) Patent No.: US 11,406,316 B2
(45) Date of Patent: Aug. 9, 2022

(54) APPARATUS AND METHOD FOR ELECTROENCEPHALOGRAPHIC MEASUREMENT

(71) Applicant: CERENION OY, Oulu (FI)

(72) Inventors: Eero Väyrynen, Oulu (FI); Jukka Kortelainen, Oulu (FI)

(73) Assignee: CERENION OY, Oulu (FI)

(*) Notice: Subject to any disclaimer, the term of this patent is extended or adjusted under 35 U.S.C. 154(b) by 562 days.

(21) Appl. No.: 15/896,203

(22) Filed: Feb. 14, 2018

(65) Prior Publication Data

US 2019/0246927 A1    Aug. 15, 2019

(51) Int. Cl.
*A61B 5/374* (2021.01)
*A61B 5/316* (2021.01)
(Continued)

(52) U.S. Cl.
CPC .............. *A61B 5/374* (2021.01); *A61B 5/316* (2021.01); *A61B 5/7225* (2013.01); *A61B 5/7257* (2013.01); *A61B 5/7264* (2013.01); *A61B 5/291* (2021.01); *A61B 5/4821* (2013.01); *A61B 5/4836* (2013.01); *A61B 5/7246* (2013.01);
(Continued)

(58) Field of Classification Search
CPC ....... A61B 5/374; A61B 5/316; A61B 5/7257; A61B 5/7264; A61B 5/7225; A61B 5/291; A61B 5/7246; A61B 5/7267; A61B 5/4836; A61B 5/4821; A61N 2005/0651; A61N 5/0622; A61N 2/006; A61N 7/00; A61N 1/36025; A61N 2007/0026;
(Continued)

(56) References Cited

U.S. PATENT DOCUMENTS 4,705,049 A * 11/1987 John ................. A61B 5/377
600/544
2005/0273017 A1* 12/2005 Gordon ............ A61B 5/048
600/544

(Continued)

FOREIGN PATENT DOCUMENTS

JP    2008-526388    7/2008
JP    2016-520375    7/2016
(Continued)

OTHER PUBLICATIONS

International Search Report dated May 14, 2019 in corresponding International Application No. PCT/FI2019/050093, 5 pages.
(Continued)

*Primary Examiner* — Devin B Henson
*Assistant Examiner* — Justin Xu
(74) *Attorney, Agent, or Firm* — Nixon & Vanderhye PC

(57) ABSTRACT

An apparatus comprises a data processing unit, which causes the apparatus to: receive at least two electroencephalographic signals of a brain of a person; form a first information about at least one of the following: phase-to-phase coupling between at least two electroencephalographic signals, phase-to-amplitude coupling between at least two electroencephalographic signals and amplitude-to-phase coupling between at least two electroencephalographic signals, the first information being related to slow waves having (Continued)

frequencies at or lower than 1 Hz; normalize the first information; and output information about the normalized first information.

20 Claims, 10 Drawing Sheets

(51) Int. Cl.
  *A61B 5/00* (2006.01)
  *A61B 5/291* (2021.01)
  *A61N 1/36* (2006.01)
  *A61N 2/00* (2006.01)
  *A61N 5/06* (2006.01)
  *A61N 7/00* (2006.01)

(52) U.S. Cl.
  CPC ......... *A61B 5/7267* (2013.01); *A61N 1/36025* (2013.01); *A61N 2/006* (2013.01); *A61N 5/0622* (2013.01); *A61N 7/00* (2013.01); *A61N 2005/0651* (2013.01)

(58) Field of Classification Search
  CPC ............ A61N 1/36064; A61N 1/36082; A61N 1/36067; A61N 1/36139; A61N 1/36031
  See application file for complete search history.

(56) References Cited

U.S. PATENT DOCUMENTS

| | | | |
|---|---|---|---|
| 2006/0167370 A1* | 7/2006 | Greenwald | G16H 20/70 600/544 |
| 2011/0066586 A1* | 3/2011 | Sabel | G16H 20/70 706/52 |
| 2014/0316217 A1* | 10/2014 | Purdon | A61B 5/7275 600/300 |
| 2015/0208940 A1 | 7/2015 | Addison et al. | |
| 2016/0287169 A1* | 10/2016 | Kortelainen | A61M 16/104 |
| 2016/0331307 A1 | 11/2016 | Purdon et al. | |
| 2017/0231556 A1 | 8/2017 | Purdon et al. | |
| 2017/0325702 A1 | 11/2017 | Kortelainen et al. | |

FOREIGN PATENT DOCUMENTS

| | | |
|---|---|---|
| WO | 2006/076478 | 7/2006 |
| WO | 2012/154701 | 11/2012 |
| WO | 2014/176356 | 10/2014 |

OTHER PUBLICATIONS

Extended European Search Report dated Oct. 8, 2021 in corresponding European Application No. 19753908.3, 8 pages.
Notification of Reasons for Rejection dated Oct. 12, 2021 in corresponding Japanese Application No. 2020-541989 (with English-language translation), 13 pages.

* cited by examiner

APPARATUS AND METHOD FOR ELECTROENCEPHALOGRAPHIC MEASUREMENT

FIELD

The invention relates to an apparatus and a method for electroencephalographic measurement.

BACKGROUND

Modern electroencephalographic (EEG) signal acquisition devices are now able to produce long time or continuous monitoring of the brain electric field potentials that directly relates to the brain function. Selecting spatial channels of interest and/or filtering desired frequency ranges from the raw EEG recordings are routinely achievable. In the Intensive Care Unit (ICU), the long-term monitoring of patient EEG is possible and, as the EEG requires relatively few resources, has many advantages to become the preferred modality for ICU bedside brain function monitoring (e.g. relatively low-cost, wireless, fast, and small device footprint). For ICU doctors, it is critical to evaluate also the status of the brain, together with the circulatory and respiratory functions of the patients, due to common occurrences of both neural dysfunctions and damage. However, continuous traditional EEG evaluation based on inspecting the basic signals is not practical or desired at the ICU level and more sophisticated signal analysis to provide the relevant information such as general and/or case specific indexes are needed.

BRIEF DESCRIPTION

The present invention seeks to provide an improvement in the measurement. The invention is defined by the independent claims. Embodiments are defined in the dependent claims.

The solutions according to the invention provide several advantages. The measured phase-to-phase, phase-to-amplitude and/or amplitude-to-phase coupling information of the EEG signals may reveal effectively how orderly the examined brain functions with respect to a normal brain.

LIST OF DRAWINGS

Example embodiments of the present invention are described below, by way of example only, with reference to the accompanying drawings, in which FIG. 1 illustrates an example an apparatus for brain function measurement;

DESCRIPTION OF EMBODIMENTS

Figure 1:
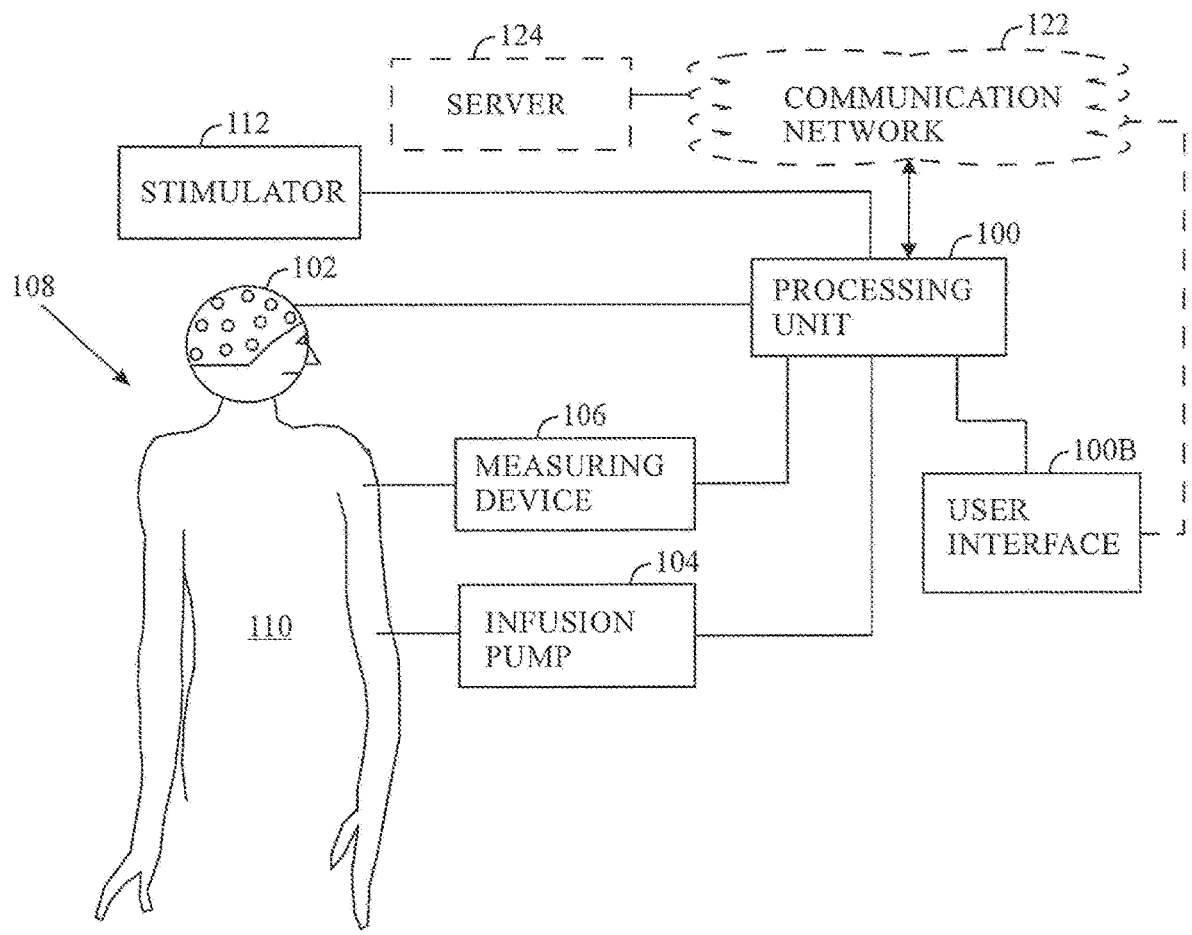

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Slow waves, the frequency of which is at or below 1 Hz (f≤1 Hz), may be considered an important EEG signatures. Based on the physiological importance of the slow waves and the possibility to test their generation with or without anesthetics in a controlled manner, it can be hypothesized that this electrophysiological phenomenon is disrupted in an injured brain. The synchronized activity of large neuronal populations as well as the delicate interaction between cortical and sub-cortical areas required in the formation of the waves can be expected to be sensitive to the brain function. It may also reveal whether the brain functions in a normal or abnormal manner.

In more detail, slow waves (equal to or less than 1 Hz) are the most important electroencephalogram signatures of non-rapid eye movement (NREM) sleep. This neurophysiologic phenomenon originates from the neurons in the neocortex and thalamus, which have been shown to exhibit slow oscillations that correlate with the slow-wave activity of electroencephalogram. Even though slow oscillations are commonly still considered to be generated exclusively in the neocortex before spreading to the other brain areas, compelling evidence highlights the thalamic contribution to their full electroencephalographic expression. The physiologic importance of the slow waves in higher cognitive function has convincingly been shown, and the lack of this electrophysiologic phenomenon has been associated with disorders of consciousness. In addition to the natural sleep, slow waves are seen in healthy individuals during general anesthesia. Originating from the same cellular and network level mechanisms as those found during NREM sleep, anesthetic-induced slow waves are considered to be a product of an unconscious brain occurring only in deep sedation/anesthesia. Recently, by using simultaneously recorded electroencephalogram and functional magnetic resonance imaging, the slow-wave activity during anesthesia was shown to be related to the isolation of the thalamocortical system from sensory stimulation and the retention of the internal thalamocortical exchange.

For this purpose, this application refers to an experiment carried out with a plurality of comatose patients of an intensive care unit (ICU) after resuscitation from out-of-hospital cardiac arrest.

The experimental protocol was approved by the institutional Ethics Committee of Oulu University Hospital which follows the Declaration of Helsinki guidelines. The patients' closest relatives were asked for an informed written consent to participate. Because of the reduced oxygen supply during the cardiac arrest, the patients potentially had suffered from hypoxic-ischemic brain injury due to which they had received therapeutic hypothermia treatment as a neuroprotective measure before the experiment. These patients generally represent a substantial diagnostic challenge as detecting the potential diffuse brain injury in the early phase of recovery is highly demanding.

Figure 2:
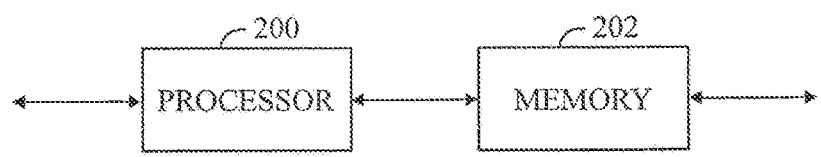
FIG. 2 illustrates an example of the processing unit comprising at least one processor and at least one memory.

Examine now an example of an apparatus for brain function measurement by means of FIG. 1. The apparatus comprises a data processing unit 100. FIG. 2 illustrates an example of block diagram of the data processing unit 100. In an embodiment, the data processing unit 100 may comprise at least one processor 200 and at least one memory 202. Their operation is based on a sequence of program commands of the computer program controlling the operation of the apparatus. The computer program may be stored in the at least one memory 202.

FIG. 1 also illustrates an electrode system 102 which provides the data processing unit 100 with at least two EEG signals of a brain of a person 110. In an embodiment, the electrode system 102 may be a part of the apparatus.

The electrode system 102 is electrically coupled or in contact with the scalp or the brain of a person 108. The electrode system 102 provides the EEG signals for the data processing unit 100. The EEG signals may be directly fed from the electrode system 102 to the data processing unit 100 or the EEG signals may first be stored in memory and the EEG data may later be fed to the data processing unit 100. The EEG signals may also be filtered before inputting to the data processing unit 100.

Electroencephalography, per se, is a recording of electrical activity of the brain. The electrical activity is measured as a voltage variation caused by the neurons of the brain tissue.

EEG signals carry EEG information in an analog or a digital form and the information can be processed and analyzed in the data processing unit 100 for determining state(s) of the brain and/or its function. A control action, a decision, presented data or a diagnosis may be based on the EEG data or the determined state(s)/function.

To record the EEG signals of person 108, the apparatus may have a plurality of channels. Each of the channels may carry an EEG signal from one electrode of the electrode system 102. The number of channels may be 19, without restricting to that. The EEG may be recorded according to the 10/20 international system using an electrode cap with Ag/AgCl electrodes as the electrode system 102. For the recording, Nicolet nEEG Modular Neurodiagnostic System with a v32 Amplifier may be used, for example. The amplifier may have a sampling frequency of 500 Hz and bandwidth of 0.053-500 Hz, for example. For the EEG recording, the patient may be sedated with an anesthetic drug substance which may follow the ICU's common practice, the patient may be stimulated with a stimulator 112 or both sedation and stimulation is done. Alternatively, the person 108 is neither sedated nor stimulated.

In general, the EEG signals may have couplings therebetween. The couplings manifest in cross-frequency and spatial signal couplings. The coupling functions may be amplitude or phase modulations, or any combination thereof. The functions may be created as groups of modulated (e.g. AM, PM or any combination thereof) communication signals measured in noisy channels (e.g. additive (AWGN) or multiplicative noise (phase noise)). The coupling functions may include one or more amplitude, phase, or frequency modulation indexes, or phase/frequency multipliers or divisors. The functions may include one or more gain (e.g. strength), time (e.g. lag), phase (e.g. shift angle) and coupling direction (e.g. causality or correlation) parameters. The functions may be presented as complex phasors with amplitude and phase functions. The detection of a function may include a coherent or non-coherent demodulator.

The phase-to-phase coupling does not depend on amplitude of the signals. Instead, the phases of the two signals having the phase-to-phase coupling can be considered phase locked with each other. When the frequencies are different, the locking may be based on n cycles of a first frequency and m cycles of a second frequency. Such coupling features may be performed with respect to any number of frequencies. The locking may also be considered n:m phase synchrony.

The amplitude-to-phase coupling indicates an interdependence between an envelope of a first signal and a phase of a second signal. A phase of the second frequency then controls or affects amplitude of the first frequency. That works also vice versa which results in phase-to-amplitude coupling.

The data processing unit 100 detects the EEG signals and forms a first information. The detection may include signal filtering. The first information may be based on a phase-to-phase coupling between the at least two electroencephalographic signals. The first information may be based on phase-to-amplitude coupling between the at least two electroencephalographic signals. The first information may be based on amplitude-to-phase coupling between at the least two electroencephalographic signals. The first information is related to slow waves having frequencies at or lower than 1 Hz. The coupling may take place between the EEG signals each of which has a frequency at or lower than 1 Hz. However, the coupling related to the slow waves may also take place between the EEG signals at least one of them having a higher frequency than 1 Hz. The phase coupling itself is thus related to the slow waves.

The data processing unit 100 then normalizes the first information. The normalization makes all EEG signal and/or slow waves commensurate, and may set them a common reference. The normalization may mean that a property of the EEG signals is set to a common value. The value may be equal to one, for example. Normalization may mean that data values are scaled to be between a lowest desired value, such as zero, and a highest desired value, such as one, for example. Normalization may also refer to distance normalization ($L^2$-norm limited within a predefined range, for example).

The data processing unit 100 finally outputs information about the normalized first comparison. The output information may be presented using a user interface such as a screen, for example. The output result may be presented visibly or audibly in the user interface 100B which is a part of the apparatus or coupled with the apparatus. The visible presentation may include alphanumeric symbols and/or a graphic representation. The user interface 100B may include a screen, a loudspeaker and/or a printer for presenting the information. The user interface 100B may also be used as an input device, the user interface including a touchscreen, a keyboard, a mouse, a microphone or the like for example. The couplings may be presented as plurality of graph trees or feature matrices.

In an embodiment, the data processing unit 100 forms the first information about the at least one phase-to-phase coupling between the at least two EEG signals. The first information may be related to the phase-to-phase coupling of slow waves between the EEG signals related to frequencies at or lower than 1 Hz. The phase-to-phase coupling may take place between signals both of which have frequencies at or lower than 1 Hz. However, the phase coupling may also exist between frequencies only one of which is at or lower than 1 Hz.

In an embodiment, the detection may include one or more artifact detection and removal (e.g. Filter, Adaptive filter, Blind Source Separation (BSS) algorithm) methods. The normalization may be a part of detection or it may be a separate operation. In this manner, noise can be compressed, for example. The detection may include a decoder (e.g. Viterbi, forward-backward search, expectation maximization algorithm). The detection may include a transformation (e.g. normalization, Principal Component Analysis (PCA), Independent Component Analysis (ICA), Wavelet transform, Empirical Mode Decomposition (EMD), Hilbert-Huang Transform (HHT), Local Linear Embedding (LLE), or Isomap). The detection may include a classifier (e.g. k-Nearest Neighbor (kNN), Linear Discriminant Analysis (LDA), Support Vector Machine (SVM), Neural Network (NN), Classification and Regression Tree (CART)). The detection may include a classification of one or more distance or similarity measures (e.g. coupling graph threes or feature matrices). The transforms are typically formed for separating information of interest into a form which is easier to process. The processing may include filtering noise, classifying features, learning, for example. The processing may include statistical methods or other methods to distinguish and/or sort independent components such as artefacts, movements of eyes (these may be omitted/deleted) or certain interesting signals (slow waves) which are selected for further processing or monitoring. Categorizers may be used to recognize the couplings. Decoders may compute and follow certain coupled signals.

In an embodiment, the detection may have on one or more thresholds. The thresholds may be selected from probability distributions, for example. The thresholds may be adaptive or include learning, and may include, for example, a signal surrogate generator (e.g. random permutation of epochs (amplitude and/or phase), large lag shifting, random split reordering of amplitude and/or phase, Fourier Transform (FT), Amplitude Adjusted Fourier Transform (AAFT), Iterative AAFT, wavelet based surrogate algorithm; a surrogate signal is a substitute signal based on mixing of signals, the surrogate signal not having a certain property such as phase coupling while other properties being as close to the original as possible), a classifier or a clustering algorithm (e.g. kNN, NN, SVM, LDA, CART, Hidden Markov Model (HMM), Gaussian Mixture Model (GMM), k-means clustering, Learning Vector Quantization (LVQ)), or a regression or an estimator (e.g. Least-Squares Estimator (LSE), Maximum Likelihood Estimator (MLE), Kalman estimator). The one or more thresholds can be used to improve signal-to noise ratio and/or limit or filter out random spikes.

In an embodiment, the data processing unit 100 may perform the first comparison as a part of normalization between the first information and a corresponding coupling template information that is based on a reference brain function. Then, a result of the first comparison is output by the apparatus.

In an embodiment, the data processing unit 100 may perform a first comparison between the first information of the phase-to-phase coupling(s) and a corresponding phase coupling template information that is based on a reference brain function. Then, a result of the first comparison of the phase-to-phase comparison is output by the apparatus.

A template may be formed by measuring at least one healthy i.e. "normal" brain. Typically a plurality of measurements of healthy brains is performed for the template. The template is a representation of a normal brain and it may include its normal variation. The template may also be called the reference brain function.

More generally, the reference brain function may represent healthy individual or an individual with epileptic activity/seizures or specific brain dysfunction. Furthermore, the reference brain function may represent the same as or other individual than the person who is under examination. Furthermore, the reference brain function may represent a measurement during natural sleep, anesthesia or while being awake.

The reference brain function may alternatively be at least partly an artificially formed representation of a normal brain function. The reference brain function may be stored in the at least one memory 202 of the data processing unit 100 and/or in a server 124 connected to a communication network 122. The data processing unit 100 retrieves the reference brain function from the memory 202 and/or from the server 124. The server 124 and the apparatus with the data processing unit 100 has access to the communication network 122 and through it also the server 124. The communication network 122 may be a local area network (LAN) or the Internet, for example. Data of the reference brain function may be collected by the apparatus and the reference brain function may be formed and stored in the memory 202 and/or in the server 124 by the data processing unit 100.

In an embodiment, the one or more coupling features may be measures of a coupling strength, a time lag of coupling, a phase of coupling, and a direction between each spatial location or frequency selection function. The coupling strength indicates how effectively one signal controls the other. The time lag refers to a delay that it takes one signal to have its effect on the other. The effect of one signal on the other may also have a phase (the effect may be completely opposite and then the phase shift therebetween is 180°, for example). The coupling may unidirectional such that one signal controls another signal in either direction. Additionally or alternatively, the coupling may be bidirectional.

The measures of coupling features may include, for example, but not limited to, modulation index, correlation, covariance, coherence, entropy measures, phase locking value (PLV), phase-lag index (PLI), heights ratio (HR), mean vector length (MVL), General Linear Model (GLM), mutual information, directed information (DI), signal-to-noise-ratio (SNR). The features may be transformed (e.g. PCA, ICA, Wavelet transform, EMD, HTT, Isomap, LLE, or within a neural network). The coupling measures may be spectral features. The features may be collected into one or more graph trees, vectors, or matrices.

Figure 3:
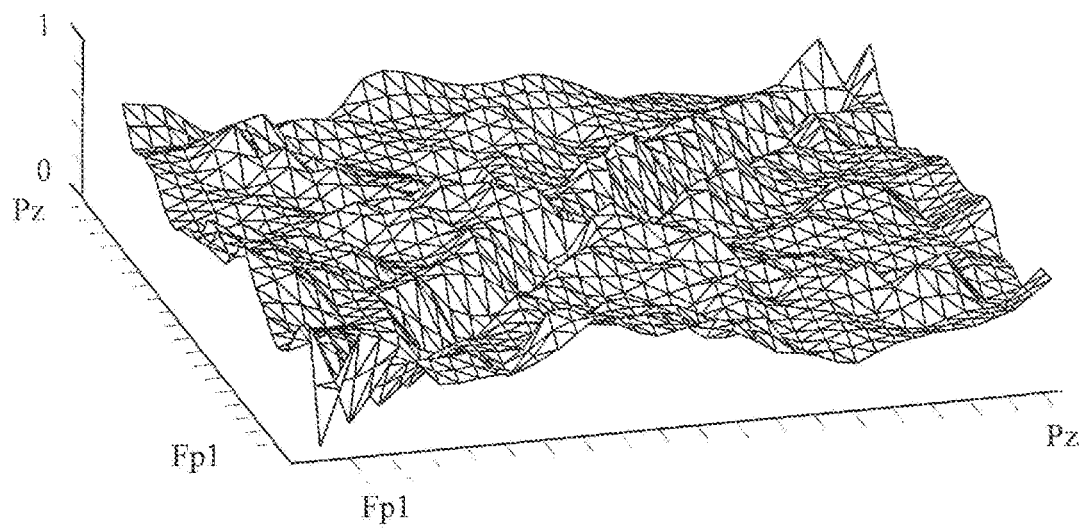
FIG. 3 illustrates an example of a reference brain function related to phase-to-phase coupling in a healthy brain.

FIG. 3 illustrates an example of the reference brain function (template) which in this example is a phase-to-phase coupling map between all electrodes Fp1, Fp2, F3, F4, C3, C4, P3, P4, O1, O2, F7, F8, T7, T8, P7, P8, Fz, Cz, and Pz used in the measurement (the electrodes are in this order in all Figures where they appear). The reference brain function may be one measurement result of a normal and/or healthy person, an average of a plurality of measurements of a normal and/or healthy person, an average of a plurality of measurements of normal and/or healthy persons or the like. The measurement may be performed repeatedly.

Figure 4:
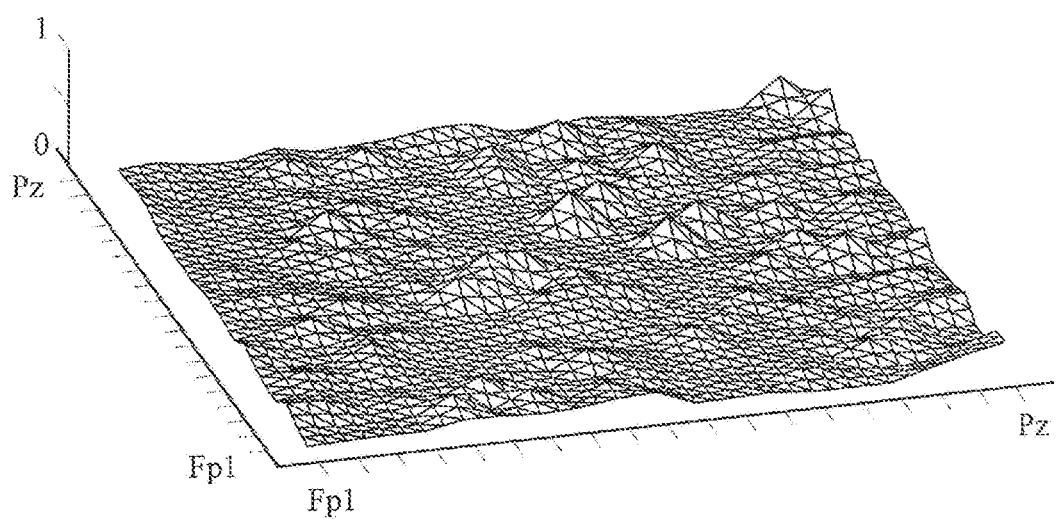
FIG. 4 illustrates an example of a difference between phase-to-phase coupling of healthy brain and the reference brain function of a healthy brain.

FIG. 4 presents an absolute difference of the phase-to-phase couplings between the corresponding reference brain function (healthy brain reference) and measured phase-to-phase couplings of a healthy brain of a person in a topographical form. As can be seen the differences between the reference and the healthy brain are not large. The absolute difference may be measured as a distance (the distance may be based on $L^2$-norm, square of Euclidian distance, some matrix norm or the like) in FIG. 4 but a similar result showing only a small difference between a healthy brain and the reference brain function would be achieved using another comparison method.

Figure 5:
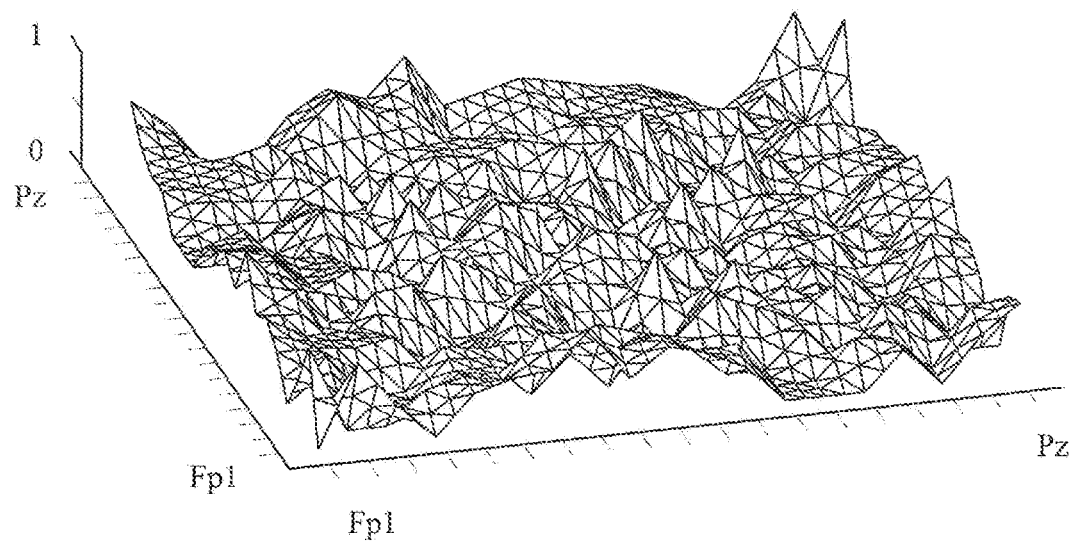
FIG. 5 illustrates an example of a difference between a phase coupling of a brain with abnormal function with a poor outcome and the reference brain function of a healthy brain.

FIG. 5 presents a difference of the phase-to-phase couplings between the corresponding reference brain function and measured phase-to-phase couplings of a brain with abnormal function of a person in a topographical form. As can be seen the differences between the reference and the brain with abnormal function are large.

Figure 6:
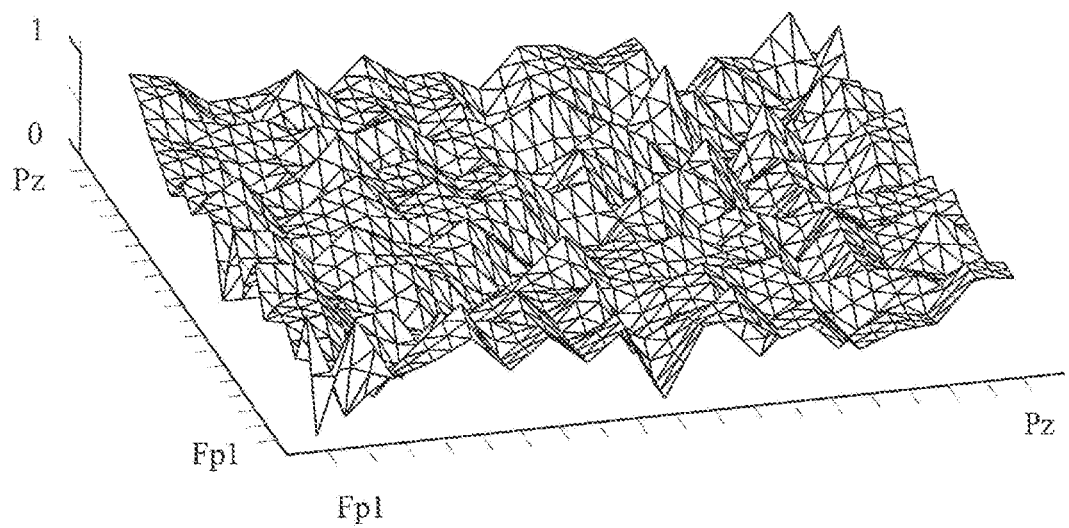
FIG. 6 illustrates an example of a difference between a phase coupling of a brain with abnormal function with epileptic seizure and the reference brain function of a healthy brain.

FIG. 6 presents an example of a topographical comparison between the phase-to-phase couplings of EEG signals of a brain having an epileptic seizure and the reference brain function (healthy brain). The phase-to-phase, phase-to-amplitude and/or amplitude-to-phase couplings of the slow waves between different areas of the brain gives another perspective to the brain than a power measurement.

Figure 7:
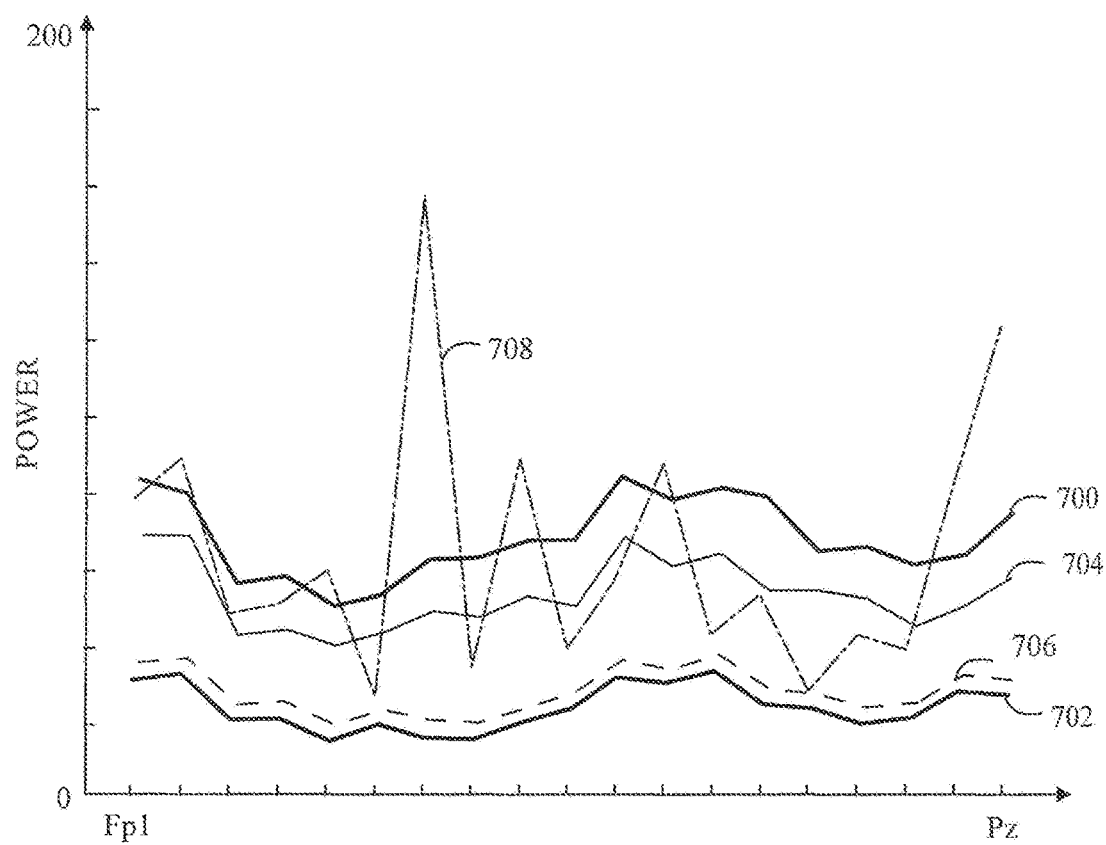
FIG. 7 illustrates an example of a reference power level curve of one or more healthy brains, a reference power level curve of one or more not-healthy brains, a power level curve of a healthy brain and a power level curve of a not-healthy brain.

FIG. 7 presents examples of a first template 700 of power levels of slow waves of the EEG signals of different electrodes/areas of a healthy brain, a second template 702 of power levels of EEG signals of different electrodes/areas of a not-healthy brain, measured signal power levels 704 of a brain with good outcome, measured signal power levels 706 of a brain with poor outcome, and measured signal power levels 708 of a brain under an epileptic seizure with a poor outcome as a line diagram. The signals have been normalized to the same scale so that they are comparable to each other. The measured signal power levels 708 of a brain under an epileptic seizure are high but the corresponding phase-to-phase coupling 706 clearly indicates that the brain deviates from a normal brain. A similar result can be achieved with the phase-to-amplitude and/or amplitude-to-phase couplings.

Figure 8:
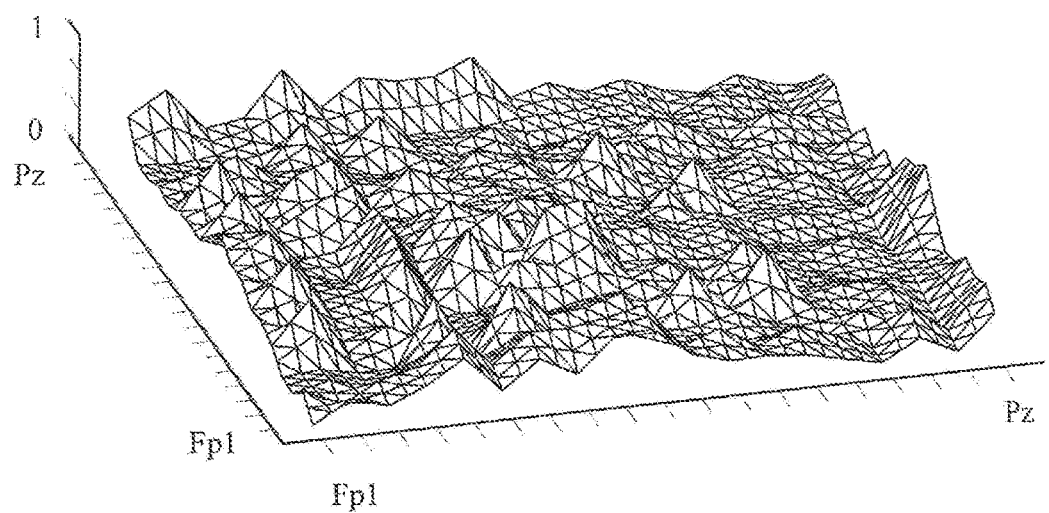
FIG. 8 illustrates an example of topographical comparison between phase-to-phase couplings of a burst suppression pattern of a brain with abnormal function and the reference brain function of a healthy brain.

FIG. 8 presents an example of topographical comparison between phase-to-phase couplings of a burst suppression pattern of a brain function and the reference brain function of a healthy brain. A comparison of the phase-to-phase couplings of the burst suppression of a healthy brain function and the reference brain function (healthy brain) has some variation which can be seen with this method.

FIGS. 3 to 6 and 8 may alternatively or additionally be presented as a heatmap, which presents values of the data matrix as colors in a graphical form.

During an epileptic activity or epileptic seizure, burst-suppression pattern or some other abnormal state, the disorder in the brain may not alter the power levels or may cause an increase in power levels of EEG signals of different areas of the brain. In this manner, comparison between power distribution of the measured areas of the epileptic/abnormal brain and corresponding areas of a normal, healthy brain may have a rather high similarity (value) i.e. small distance(s), for example. It could thus be misinterpreted that the couplings between different areas are at least fairly normal which might even be thought a normal state of the measured brain. However, the phase-to-phase, phase-to-amplitude and/or amplitude-to-phase couplings between different areas of the brain typically deviate from normal during a dysfunction, which reveals the disorder with respect to the normal brain easily. The dysfunction may be an epileptic activity or seizure, for example. The power measurement may still reveal disorders although not as effectively as or in a similar manner to the phase-to-phase, phase-to-amplitude and/or amplitude-to-phase coupling measurement(s).

In an embodiment, the data processing unit 100 may form a second information about power of at least one EEG signals. The second information may include powers of the measured channels (see FIG. 7). The second information may include powers related to areas/electrodes of the brain. Power of an area of the brain may include powers of a plurality measured channels. The power of an area may be an average power or a weighted average power, for example. Then the data processing unit 100 may perform a second comparison between the second information and a corresponding power template information that is based on a reference brain function (healthy or not-healthy brain). Finally, the data processing unit 100 may output information about the second comparison. The output may be presented visibly or audibly in the user interface 100B. The user interface 108B may present the output in a similar manner to that related to the phase-to-phase, phase-to-amplitude and/or amplitude-to-phase coupling measurement(s).

Figure 9:
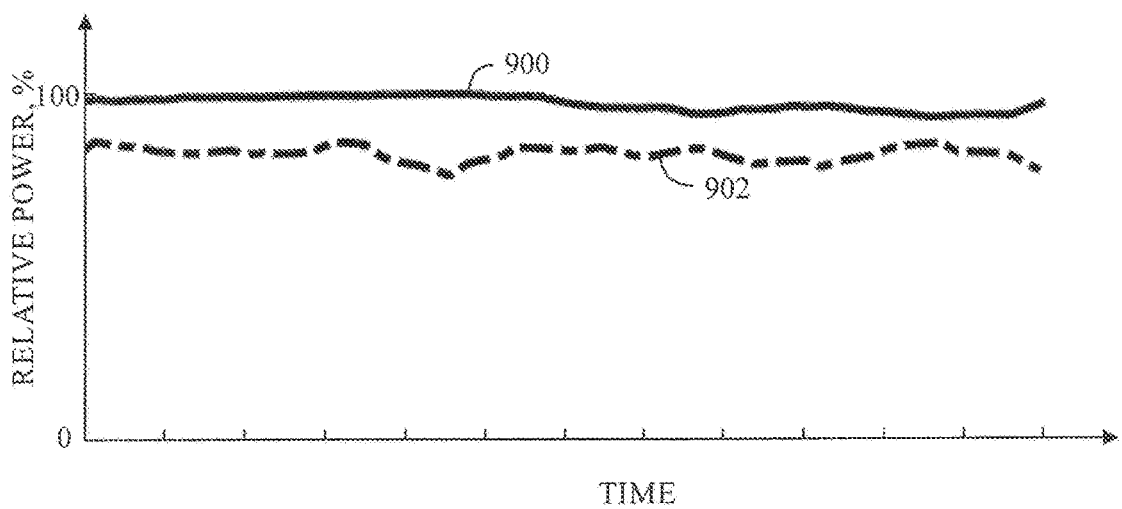
FIG. 9 illustrates an example of a curve of a power level of the first reference brain function and a curve of a power measurement of a not-healthy brain.
Figure 10:
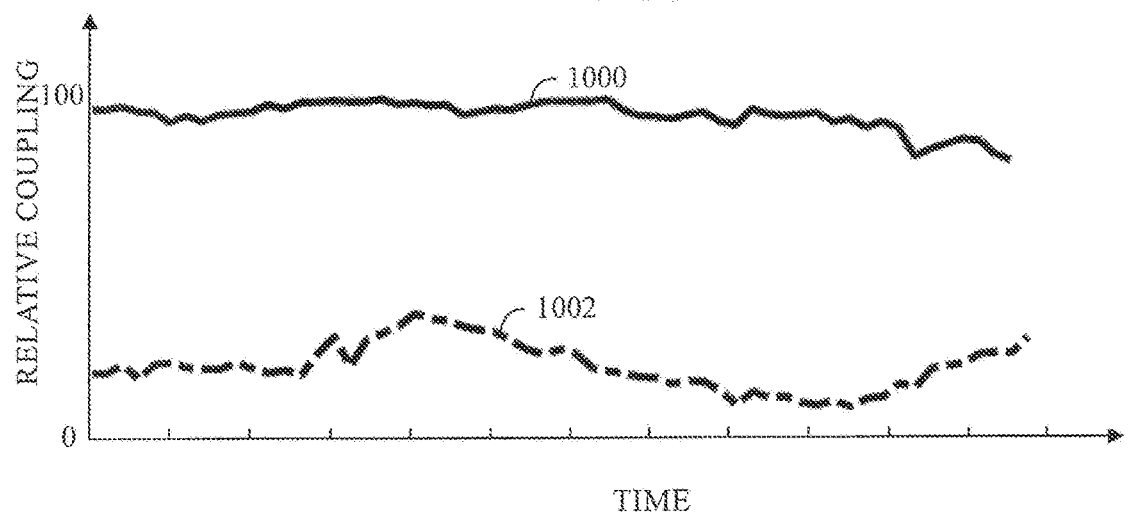
FIG. 10 illustrates an example of a curve of the phase coupling of the first reference brain function and a curve of a phase coupling of the not-healthy brain.
Figure 11:
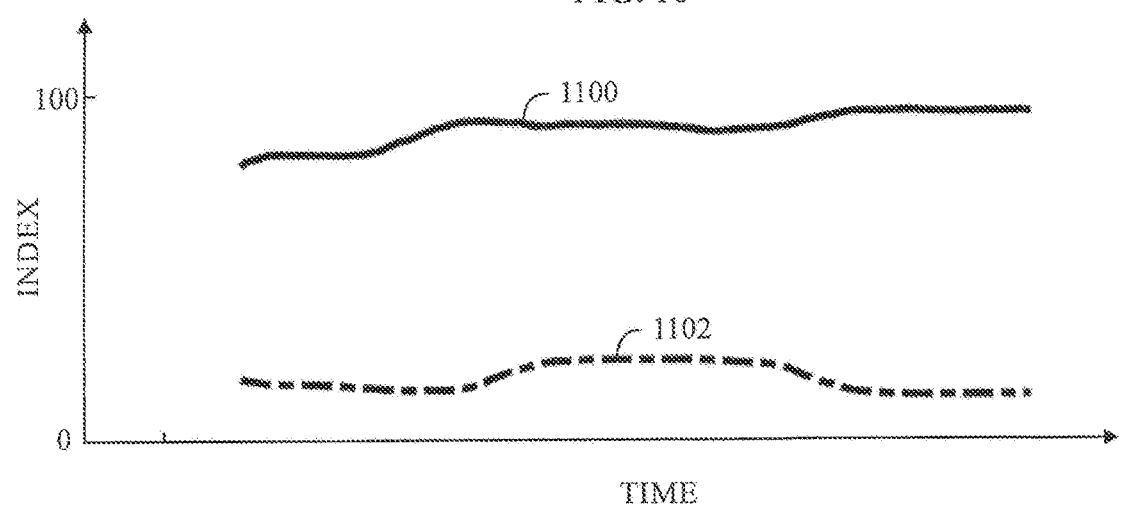
FIG. 11 illustrates an example of a curve of a combination of a power level and the phase coupling of the first reference brain function and a curve of a power and phase coupling measurement of a not-healthy brain.

In an embodiment illustrated in FIGS. 9, 10 and 11, the data processing unit 100 may combine the first information and the second information. The number of measurements of the powers and the number of measurements of the phase-to-phase, phase-to-amplitude and/or amplitude-to-phase couplings may be the same or different. Irrespective of their number, the measurements may be combined in a deterministic manner. The values of the power and the phase-to-phase, phase-to-amplitude and/or amplitude-to-phase coupling may be summated or averaged with or without weights together, for example.

In FIG. 9, an example of a measurement of a power level 900 of brain function of a healthy brain and a measurement of a power level 902 of a brain with abnormal function are presented as a function of time. The power level 902 of the healthy brain approaches the relative level 100. In FIG. 10, an example of phase-to-phase coupling 1000 of a brain function of the healthy brain and a measurement 1002 of phase-to-phase couplings of a brain with abnormal function are presented as a function of time. In this example, the level 1002 of the not healthy brain approaches 0 because of scaling and multiplication using a sigmoid function. The phase-to-phase coupling 1002 of the healthy brain, in turn, approaches the relative coupling 100 when the EEG signals are processed in a similar manner. In the examples of FIGS. 9 and 10, it can be seen that the power level may refer to a good outcome, because the power curves are close to each other, but the phase-to-phase coupling (or either the phase-to-amplitude or the amplitude-to-phase coupling) show that the outcome of the measured brain is poor. In FIG. 11, the reference brain functions 900 and 1000 of FIGS. 9 and 10 have been combined in order to form a curve 1100 of a combined reference index. In a similar manner, the measurements 902 and 1002 have been combined in order to form a curve 1102 of a combined measurement index. In FIG. 11, the poor outcome is clear because the coupling index related to the phase couplings in the slow waves is so low. The coupling index curve 1102 related to the phase couplings in the slow waves may be low i.e. below a threshold continuously. The index may be formed on the basis of feature or distance calculations. For example, a maximum or weighted distance, an average of distances or using pseudometrics (Kullback-Leibler (KL) divergence, for example) from the template. The result may be scaled to have a desired range between an upper limit and a lower limit (from 0 to 10 or from 0 to 100, for example) using a membership/activation function, such as Softmax or sigmoid, and multiplication with a scalar.

Other way to form the indices is to use regression on the variables of which have been scaled in a desired range. The regression may be a linear regression (GLM=Generalized Linear Model), a nonlinear regression (SVR=Support Vector Regression, for example), or other categoriser such as SVM (Support Vector Machine), NN (Neural Network), kNN (k-Nearest Neighbor), and it may directly utilize the features. The result may be continuous or discrete in an ordinal manner. Alternatively, the result may be arbitrary implying seriousness (classes: normal, slightly deviating, deviating, strongly deviating and isoelectric), for example.

More than one different kind of indices may be combined using fuzzy logic, for example. Another possibility is to use fusion of classifiers. In both cases, scaling may be performed.

In the examples of this application, the indices are formed separately for power and the couplings using average distances between the measurements and a suitable template. The indices have been scaled in the range 0 to 1 and in the user interface 0 to 100. Then the indices have been multiplied with each other.

The data processing unit 100 may perform a combined comparison between the combined information and a corresponding combined template information that is based on the reference brain function. Then the data processing unit 100 may output information about the combined comparison. The output may be presented visibly or audibly in the user interface 100B. The user interface 108B may present the output in a similar manner to that related to the phase-to-phase, phase-to-amplitude and/or amplitude-to-phase coupling measurement(s).

In an embodiment, the first information associated with areas of the brain may be presented on a map of the skull on the basis of the location of the electrodes such as Fp1 to Pz instantly or as a function of time. Values of the first information may be represented using color scales, for example. In a similar manner, the first and second information associated with areas of the brain may be presented in a combined or separate manner on a map of the skull. The values of the combined or separate first and second information may be represented using color scales, for example.

In an embodiment, the data processing unit 100 may receive the at least two EEG signals of the brain of the person 110 who is, or is at least expected to be, under influence of at least one in the following list: epileptic activity, brain dysfunction, neural injury, sleep, and one or more non-zero amounts of anesthetic drug substance. The epileptic activity may include an epileptic seizure. The sleep may refer to natural sleep or an anesthetic drug substance assisted sleep.

In an embodiment, the data processing unit 100 may estimate whether the person 110 is under the influence of the at least one in said list on the basis of the first comparison, and present a result of the estimation. The output may be presented visibly or audibly in the user interface 100B.

In an embodiment, the data processing unit 100 may estimate whether the person 110 is under the influence of the at least one in said list on the basis of the second comparison, and present a result of the estimation. The output may be presented visibly or audibly in the user interface 100B. The estimation and output may refer to one or more determined influences which are considered certain. Alternatively, probabilities of the one or more influences may be estimated and output.

In an embodiment, the data processing unit 100 may predict a neurological function level of the person 110 on the basis of the first comparison. In an embodiment, the data processing unit 100 may predict a neurological function level of the person 110 on the basis of both the first comparison and the second comparison. In an embodiment, the data processing unit 100 may predict a neurological function level of the person 110 on the basis of the comparison related to the combination of the first information and the second information.

In an embodiment, the data processing unit 100 may predict a further development of the neurological function level of the person 110 towards a good or better outcome if a difference between the first information and the phase coupling template information is smaller than a first determined threshold. The data processing unit 100 may predict the further development of the neurological function level of the person 110 towards a poor or worse outcome if a difference between the first information and the phase coupling template information is larger than a second determined threshold. The differences may be in absolute values i.e. no negative differences are used. The first and second thresholds may be the same or they may be different. The first threshold is equal to or smaller than the second threshold. The thresholds may be based on a theory, a simulation or experience.

In an embodiment, the data processing unit 100 may predict a further development of the neurological function level of the person 110 towards a good outcome if the difference between the first information and the phase coupling template information is smaller than the first determined threshold and the power level of the second information is higher than a third determined threshold. The data processing unit 100 may predict a further development of the neurological function level of the person 110 towards a poor outcome if the difference between the first information and the phase coupling template information is larger than the second determined threshold and the power level of the second information is lower than a fourth threshold.

In an embodiment, the data processing unit 100 may predict a further development of the neurological function level of the person 110 towards a good outcome if the difference between the first information and the phase coupling template information is smaller than the first determined threshold and the difference between the second information and the corresponding power template information is smaller than a fifth determined threshold. The data processing unit 100 may predict a further development of the neurological function level of the person 110 towards a poor outcome if the difference between the first information and the phase coupling template information is larger than the second determined threshold and the difference between the second information and the corresponding power template information is larger than a sixth determined threshold.

The thresholds may depend on the measurement devices, patients, type of measurement (scalp/brain), electrodes (number of them, type, coupling to skin/brain) etc. However, a person skilled in the art can easily determine the thresholds from the first to the sixth that work on the basis of even one calibration measurement. With only a few (5 to 10) more calibration measurements, the thresholds can be made more accurate. With even more calibration measurements, the thresholds can be made as accurate as possible.

In an embodiment, the data processing unit 100 may separate phase and amplitude information of the at least two EEG signals for the determination of the couplings. The separation may be based on a phase separating convolution transform, for example. An example of the phase separating convolution transform is the Hilbert transform. However, any other transform that results in the separation of the phase and envelope/amplitude of a signal may be used. Such a transform that may utilize Discrete Energy Separation Algorithms (DESAs) that, in turn, utilize the Teager Kaiser Energy Operator (TKEO), can be produced in various ways. The transform may be produced on the basis of Infinite Impulse Filter (IIR), Fourier transforms using the Heaviside step function and the sign function, or estimated with Finite Impulse Response (FIR) filters as is clearly implied by the definition with convolution, for example. In an embodiment, the phase-amplitude demodulation may affect the choice of the phase separation transform.

In an embodiment, the data processing unit 100 may form the first information on the basis of at least one of the following: information theoretical measures, phase multipliers, demodulation, probability density estimation, bivariate measures, correlation, multivariate causality measures, and coupling fingerprints. The phase multipliers, such as phase locking multipliers may be the coefficients with which the couplings have been detected.

Information theory gives bounds for what can be achieved and how information flows may be modeled to form statistical inference tools to assess, especially causal inference relations and finally construct connection estimates as graphs. Key concepts related to the EEG signal inference here are entropy, KL divergence (information gain), mutual information, directed information, correlation and causality, topology, and complexity. Signal analysis also leverages tools and concepts under the broad topics of machine learning and artificial intelligence in general.

In information theory, two signals are defined as random processes $X^n = \langle x_1, x_2, \ldots, x_n \rangle | x_n \in \mathbb{R}$ and $Y^n = \langle y_1, y_2, \ldots, y_n \rangle | y_n \in \mathbb{R}$.

Shannon entropy of an uncorrelated source is $$H(X^n) = -\sum_{x \in X^n} p(x) \log(p(x)).$$

With correlation, the mutual information is $$I(X^n; Y^n) = \sum_{i=1}^{n} I(X^n; Y_i | Y^{i-1}) =$$

$$\sum_{y \in Y^n} \sum_{x \in X^n} p(x, y) \log\left(\frac{p(x, y)}{p(x)p(y)}\right) = H(Y^n) - H(Y^n | X^n),$$

where $H(Y^n|X^n)$ is the conditional entropy, and with causal influence, the DI (Directed Information) is $$I(X^n \to Y^n) = \sum_{i=1}^{n} I(X^i; Y_i | Y^{i-1}) = H(Y^n) - H(Y^n \| X^n),$$

where $H(Y^n\|X^n)$ denotes the causal entropy.

Signal phase couplings may be modeled as a source and a modulated signal pair, i.e. single sideband modulated (SSB) for phase-phase coupling, or Amplitude Modulated (AM) for a phase-amplitude coupling, sequences that can be preferably analyzed with demodulation at a chosen baseband, e.g. slow wave couplings at [0 1] Hz, but also at unique multipliers $$z = \frac{m}{n}$$

thereof. Couplings with phase multipliers n, m may also correspond to modulated signals of various types (e.g. upper SSB, AM, CW, depending on the definition of the phase components). A phase coupling between signals $x_i$ and $x_j$ is defined generally as $$|n \cdot \varphi_{x_i}(t) - m \cdot \varphi_{x_j}(t)| = |\Delta \varphi(t)| \leq M, \forall t \in \mathbb{R} ; n, m \in \mathbb{N},$$

where M is a constant defining the quality of the phase coupling difference. If $\Delta\varphi(t)=M$, the coupled signals are perfectly coupled (M=0 means the signals are identical after multiplications). If $|\Delta\varphi(t)| \leq M$, the signals are in phase entrainment, which may be the case in the presence of noise and/or for chaotic coupled signals.

Often in biological systems the multipliers of interest are restricted to n=1 and m=1, however, multiplier connections of higher frequency ranges may be of interest, especially when defining phase couplings between a source signal phase and a modulated target signal amplitude at a higher frequency band.

Phase multipliers may be explained as follows.

$$r \leq \frac{(d-c) + z(b-a) - |d-zb| - |za-c|}{(d-c) + z(b-a) + |d-zb| + |za-c|}, \text{ where } z = \frac{m}{n}$$

is the multiplier, source signal bandwidth is $[a\ b]=[f_1\ f_2]=BW_{x_i}$, target signal bandwidth is $[c\ d]=[f_3\ f_4]=BW_{x_j}$, and $1 \geq r \geq 0$ is the band overlapping ratio for the multipliers. The phase noise increase for the multiplications is then up to a chosen threshold level:

$$N_{\Delta\varphi} = n \cdot N_{\varphi x_i} + m \cdot N_{\varphi x_j} \leq N_{threshold}.$$

Now by selecting $P_{inband} = r \cdot P$, $P_{outband} = (1-r) \cdot P$, where signals are assumed uniformly distributed in the corresponding bandwidths and assuming uncorrelated phase noises $N_{\varphi x_i}$ and $N_{\varphi x_j}$ we can estimate the change in SNR:

$$SNR_{\Delta\varphi} = 10 \cdot \log\left(\frac{P_{inband}}{P_{outband} + N_{\Delta\varphi}}\right) \sim 20 \cdot \log\left(\frac{r}{(1-r) + (n+m-1) \cdot N_{\Delta\varphi}}\right)\bigg|$$

$$[N_{\varphi x_i} \approx N_{\varphi x_j}] \to \frac{(n+m-1) \cdot N_{\Delta\varphi}}{r} \leq 40 \bigg| SNR_{threshold} \approx -32 dBc,$$

where $\Delta SNR_{threshold}$ is a chosen maximum allowed decrease in SNR due to phase noise increase and/or signal loss, caused by a selection of multipliers and/or limited bandwidth overlap. Note that this is an example threshold and the value may also be different, such as −30 dBc or −40 dBc, for example. Now, a unique range of $$z = \frac{n}{m}$$

candidates can be formed inside the operating threshold. For example, choosing $\Delta SNR_{threshold} = -12$ dBc, $r \geq 0.5$, $N_{\Delta\varphi} = 0.5$ we get $n+m \leq 9 | r=1$ and $n+m \leq 5 | r=0.5$. Then and m candidates can be produced e.g. by a vector outer product $1/\langle 1, 2, \ldots, n \rangle \otimes \langle 1, 2, \ldots, m \rangle$ to get a raw z candidate matrix Z. The candidate matrix $$Z = \frac{m}{n}$$

will contain duplicates $$\left(e.g.\ 2 = \frac{2}{1} = \frac{4}{2}\right)$$

that may be removed, e.g. by sorting the vectorized candidate matrix and then removing subsequent identical values (also values less than one may be discarded immediately if the target bandwidth is higher and separate from the source bandwidth), and then returning to original matrix. If the bandwidths $BW_{x_i}$ and $BW_{x_j}$ do not map with the candidate z multiplications, the corresponding fractions with too low r may be removed. The n and m candidates may then be selected as the matrix rows and columns containing valid z values. One can note that most phase multiplier candidates will not align naturally with the traditionally defined EEG bandwidths (i.e. delta, alpha, theta, gamma). Also, the set of multipliers of interest can be pre-calculated and selected offline for applications including learning structures.

A histogram based approach may be used to simplify the estimation of the distributions of random variables. Using a count function $m_k$ a distribution P is defined with random processes $X^n$ and $Y^n$ measured with the functions $f, g: \mathbb{R} \to \mathbb{R}$.

$$P(k) = m_k(f(x_i), g(y_i)) | [x_i \in X^n, y_i \in Y^n]$$

such that the sample size N and bin size K may be chosen as $N = \Sigma_{k=1}^K m_k$ and $K \sim \sqrt[3]{\sqrt{N}}$.

If we choose sampling rates $F_s = 100$ Hz → 250 Hz and time windows t=30 s → 60 s with an aim to select evenly distributed bins we get, for phase binning, (i.e. 360=2*2*2*3*3*5) 360° is divisible by: 2, 3, 4, 5, 6, 8, 9, 10, 12, 15, 18, 20, 24, 30, 36, 40, 45, 60, 72, 90, 120, or 180), or using powers of two divisions in radians (i.e. $2\pi/2^n | n \in \{1,2,3, \ldots, 8\}$), we get reasonable power of two divider powers as 2, 4, 8, 16, 32, 64, 128, or 256. To support Fast Fourier Transform (FFT) calculations efficiently a power of 2 sample rate is also preferable (e.g. $N=2^n | n \in \{12,13\}$). Now we get following options of N samples produced by the combinations of $F_s$ and t choices (with orders of magnitudes shown):

$$\Rightarrow N = 3000(3*10^3) \to 2^{12}(\sim 4*10^3) \to 6000$$
$$(0.6*10^4) \to 7500(0.75*10^4) \to$$
$$2^{13}(\sim 0.8*10^4) \to 15000(1.5*10^4)$$

and for the corresponding candidates of K bins in degree format (in radian format and/or N is a power of 2):

$$\Rightarrow K \sim 15(16) \to 18 \to 20 \to 30(32)$$

Similarly, we may derive for amplitude bins, using a reasonable value range and resolution, suitable K candidates.

A probability distribution may also be estimated (e.g. as a continuous function or with discrete quantization levels such as K bins) to form a probability density estimate using one or more other methods such as kernel density estimation, parametric density modeling (e.g. GMM), and Monte Carlo type methods (e.g. sampling or bootstrapping). The densities may be modeled also in a multi-feature (i.e. multi-dimensional) setting using tools such as kernel embedding or dimensionality reduction methods to provide a set of distributions of interest corresponding to a low-dimensional set of transformed features (e.g. to apply a supervised selection or transformation of the original feature space).

Bivariate measures of couplings, and causality, can be derived for features as follows.

The HR (Heights Ratio) measuring the unevenness of the distribution (e.g. the bins of the histogram estimate) is:

$$HR(P) = \frac{\max(P) - \min(P)}{\max(P)}.$$

Entropy is then $$H(P) = -\sum_{k=1}^{K} P(k) \log[P(k)],$$

the KL (Kullback-Leibler) divergence with distribution Q(k) is $$D_{KL}(P, Q) = \sum_{k=1}^{K} P(k) \log\left[\frac{P(k)}{Q(k)}\right],$$

and, assuming a uniform distribution (i.e. no coupling) U we also get $$D_{KL}(P,U)=\log(N)-H(P).$$

Using $D_{KL}(P, U)$ we get the Modulation Index (MI) measure $$MI(P, U) = \frac{D_{KL}(P, U)}{\log(N)}.$$

Also, directly from the phase differences, the PLV (Phase Locking Value)

$$PLV = \left|\frac{1}{N}\sum_{n=1}^{N} e^{i\cdot\Delta\varphi(n)}\right|,$$

where $\Delta\varphi(n)$ is the phase difference of the signals after applying any multipliers.

Many other features such as GLM (General Linear Model), MVL (Mean Vector Length), Bicoherence, the information theoretic measures such as DI etc. may be used to estimate phase couplings.

For signals x and y the cross-correlation (*), using the convolution (*) is $$C(\tau)=x(t)*y(t)=x(t)*y*(-t),$$

where $x^*(-t)$ is denotes conjugated and time-reversed signal, and the autocorrelations follow simply, here only for the signal x, $$R(\tau)=x(t)*x(t)=x(t)*x^*(-t).$$

In the frequency domain using the Fourier transform we get $X(f)=\mathcal{F}[x(t)]$ and $Y(f)=\mathcal{F}[y(t)]$. In the frequency-domain, the corresponding qualities for cross-correlation and autocorrelation $S_{xy}(f)$ and $S_{xx}(f)$, i.e. the cross-spectral density and the power spectrum, respectively, are now multiplications of transformed functions and complex conjugated transformed functions with the assumption that the signals in the frequency-domain are Hermitian functions (i.e. guaranteed for a Fourier transform of a real valued signal) allows $S_{xy}(f)=X(f)\cdot Y^*(f)$ and $S_{xx}(f)=X(f)\cdot X^*(f)$, respectively.

The time-domain versions follow in a straightforward fashion, by using the inverse Fourier transform, $R(\tau)=\mathcal{F}^{-1}[S_{xx}(f)]$ and $C(\tau)=\mathcal{F}^{-1}[S_{xy}(f)]$, respectively. For discrete-time signals, the Discrete Fourier Transform (DFT) and the Inverse Discrete Fourier Transform (IDFT), i.e. in practice the Fast Fourier Transform (FFT) and the Inverse Fast Fourier Transforms (IFFT) correspondingly, are used.

The "analytic" correlation can now be constructed, here for cross-correlation only, $$C_a(\tau)=C(\tau)+\iota\cdot\hat{C}(\tau),$$

where $\hat{C}(\tau)$ is the 90°

$$\left(i.e. \frac{\pi}{2}\right)$$

shifted cross-correlation. In practice, the analytic correlation for a signal pair may be constructed directly in the frequency-domain before returning to the time-domain, i.e. defining the analytic signal of the cross-correlation by e.g. using an approximation of the Hilbert transform in the frequency-domain. Alternatively, one can construct all the required correlations from the corresponding analytic signals of x(t) and y(t) (or depending on the coupling types one is interested in, phase functions, analytic normalized envelope functions, or any phase shifted or modulated version derivatives thereof), by taking the corresponding real and imaginary parts of the analytic signal functions (or derivatives) and separately produce the correlations and phase shifted correlations of interest (e.g. simple convolution). Or, more likely, working all the time in the frequency-domain, since, for cross-correlation, $$C(\tau)=x(t)*(y(t)*h(t))=(x(t)*y(t))*h(t)=(x(t)*y^*(-t))*h(t),$$

where h(t) is a kernel. In the frequency-domain the kernel convoluted cross-correlation $S_{xy}^h(f)$ becomes then $$S_{xy}^h(f)=X(f)\cdot Y^*(f)\cdot H(f)=S_{xy}(f)\cdot H(f),$$

where $H(f)$ is the Fourier transform of the kernel h(t). Now, for example, to perform Hilbert transformation on the cross-correlation $H(f)$ can be chosen as the Heaviside step function and the sign function (i.e. a finite length estimate filter), and any other FIR filters (e.g. frequency selection, envelope estimation, or phase estimations) may be implemented by choosing the $H(f)$ as the Fourier transform of the filter coefficients (i.e. filter impulse response), or any cascade combination thereof. The practical implementation of filtering for computationally and memory efficient continuous operation may then be realized with circular buffers using either overlap-save or overlap-add algorithms for construction of the output buffers depending on which gives better efficiency as dictated by the selected analysis window, FFT, and filter lengths. Using the Hilbert transform we can get the complex "analytic" cross-correlation $C_a(\tau)=\mathcal{F}^{-1}[S_{xy}^a(f)]$, where $$S_{xy}^a(f) = \begin{cases} 2X(f)Y^*(f), & f > 0 \\ Y(0)X^*(0), & f = 0 \\ 0, & f < 0 \end{cases}$$

is the analytic cross-spectrum. For finite N length discrete-time signals the relevant zero-padded 2N length (i.e. to produce a cross-correlation sequence of 2N−1 values) DFT equations are:

$$X(k) = T\sum_{n=0}^{N-1} x(n)e^{-\iota 2\pi kn/2N}$$

$$Y(k) = T\sum_{n=0}^{N-1} y(n)e^{-\iota 2\pi kn/2N}$$

$$S_{xy}^a(k) = \begin{cases} X(0)Y^*(0), & k = 0 \\ 2X(k)Y^*(k), & 1 \leq k \leq N-1 \\ X(N)Y^*(N), & k = N \\ 0, & N+1 \leq k \leq 2N-1 \end{cases}$$

$$C_a(n) = \frac{1}{2NT}\sum_{k=0}^{2N-1} S_{xy}^a(k)e^{\iota 2\pi nk/2N}$$

When the correlations of interest between chosen signal component have been calculated, using the complex "analytic" correlation we can establish peak correlations $c_{max}$, group time delay $\tau_d$, and instantaneous phase differences $\varphi_{\tau_d}$ by equations:

$$c_{max} = \max_\tau |C_a(\tau)|$$

$$\tau_d = \operatorname{argmax}_\tau |C_a(\tau)|$$

$$\varphi_{T_d} = \arg[C_a(\tau_d)] = \operatorname{atan2}(\mathcal{I}\{C_a(\tau_d)\}, \mathcal{R}\{C_a(\tau_d)\}),$$

where $\tau$ (i.e. the lag) can be chosen to be $\tau \geq 0$ to satisfy the time-criterion of causality (i.e. only past can impact the future), however, a correlation at a negative lag, $\tau_d < 0$, could also be interpreted so that causality may exist in the reverse direction. It is relevant to find correlation maximums for both directions for multisensory signal data due to a presence of possible feedback networks and the fact that neither signal might be original information sources but the found cross-correlations are instead only by cascading and/or proxy. In those cases, correlation can be seen both ways, however, this does not imply causality may exist both ways (but could suggest that a cyclic causation exists). Therefore, if the correlation analysis is to be done between all signals and components of interest thereof, each correlation can be seen containing two directions and both negative and positive lags can be used to calculate the correlation, group delay, and phase difference values. Depending on the signals of choice and due to signal component selections (i.e. modulations) and frequency selection functions (i.e. filters) some directions may be unlikely to contain real correlations. Also, similar analysis of the autocorrelation functions is of interest due to possible periodicity (e.g. due to signal intrinsic quality or network cascade/proxy connections).

The connection of correlation to the signal-to-noise ratio (SNR) with a clean signal (reference signal) and a noisy corrupted signal is:

$$SNR^{ref} = \frac{P}{N_o} = \frac{R^2}{1-R^{2'}}$$

where P is the signal power, $N_0$ is the noise power, and R is the cross-correlation. Similarly, the SNR for two signals added with an equal amount of uncorrelated noise (measured signals) is $$SNR^{measured} = \frac{P}{N_o} = \frac{R}{1-R}.$$

As a straight calculation of the cross-correlation is heavily influenced by any phase and lag differences, estimates for a coupling SNR needs to be taken at the maximum cross-correlation peaks. We then get the corresponding SNR estimates at maximum correlation, in dB $$SNR^{ref}_{\tau_d,\varphi_{\tau_d}}(dB) = 10 \cdot \log_{10} \frac{c_{max}^2}{1-c_{max}^2}, \quad SNR^{measured}_{\tau_d,\varphi_{\tau_d}}(dB) = 10 \cdot \log_{10} \frac{c_{max}}{1-c_{max}}.$$

Multivariate causality measures can be derived and are based on a basic principle where Channel i,j causality testing is done using all channel information to predict a channel i together (i.e. conditioned on all the available past information). Then, a comparison is made to a set where a channel j is removed (i.e. conditioned without channel j past information). If a significant drop in the used causality measure is observed, then a causality link may be established between channels i,j. Such links may be collected in a matrix or graph tree structures and used as features or in addition to other features.

Causality measures, and couplings, may be calculated as linear multivariate autoregressive (AR) model-based estimators, e.g. Granger causality and associated methods such as Directed Transfer Function (DTF), Partial Directed Coherence (PDC) and derivative methods thereof. Also, nonlinear Information theoretic model-based measures such as the directed information, transfer entropy or conditional transfer entropy may be used.

Multivariate causality graph constructions may contain similar direction, lag, phase difference and measured coupling magnitudes structures as the bivariate versions. Also, significant causality and coupling structures may be identified with similar methods, for example, with hypothesis testing using Monte Carlo methods such as bootstrapping and surrogates.

Coupling structures between multiple measured signals, i.e. coupling fingerprints, may be presented as matrices. For example, in a bivariate linear case using time-domain cross-correlation, modulation index, and heights ratio as the measures, we proceed followingly. Assuming real transfer functions $f$, $g$, channels i,j, and sample indexes m, n such that $$f,g: \mathbb{R} \to \mathbb{R} ; i,j \in \mathbb{N} ; m,n \in \mathbb{Z},$$

we get signal components of interest $u_{f,x_i}(n)$ and $u_{g,x_j}(n)$ from measured signals $x_i(n)$ and $x_j(n)$ so that $$u_{f,x_i}(n) = f(x_i(n)) \text{ and } u_{g,x_j}(n) = g(x_j(n)).$$

From the components, cross-correlations are then defined as $$C^{i,j}(m) = u_{f,x_i}(n) * u_{g,x_j}(n),$$

and the "analytic" cross-correlations are $$C_a^{i,j}(m) = C^{i,j}(m) + \iota \cdot \hat{C}^{i,j}(m).$$

Maximum cross-correlation peak magnitudes are then $$c_{max}^{i,j} = \max_m |C_a^{i,j}(m)|,$$

the time lags for maximum correlation peaks are $$\tau_d^{i,j} = \operatorname{argmax}_m |C_a^{i,j}(m)| \bigg| m \geq 0,$$

and the phase differences are $$\varphi_{\tau_d}^{i,j} = \arg[C_a^{i,j}(\tau_d^{i,j})].$$

Using vector and matrix notations assuming the measured signals $x_i(n)$ and $x_j(n)$ correspond to random processes $X_i^n$, $X_j^n$ at a given measurement interval we get the maximum cross-correlation peak magnitude matrix as $$C(X_i^n, X_j^n) = \begin{pmatrix} c_{max}^{1,1} & \cdots & c_{max}^{1,j} \\ \vdots & \ddots & \vdots \\ c_{max}^{i,1} & \cdots & c_{max}^{i,j} \end{pmatrix},$$

the measured lag matrix as $$T_d(X_i^n, X_j^n) = \begin{pmatrix} \tau_d^{1,1} & \cdots & \tau_d^{1,j} \\ \vdots & \ddots & \vdots \\ \tau_d^{i,1} & \cdots & \tau_d^{i,j} \end{pmatrix},$$

and the measured phase matrix as $$\Phi_{\tau_d}(X_i^n, X_j^n) = \begin{pmatrix} \varphi_{\tau_d}^{1,1} & \cdots & \varphi_{\tau_d}^{1,j} \\ \vdots & \ddots & \vdots \\ \varphi_{\tau_d}^{i,1} & \cdots & \varphi_{\tau_d}^{i,j} \end{pmatrix}.$$

Now, using the lag and phase information, and analytic representation of the signal components ($u_{f,x_i}^a$ and $u_{g,x_j}^a$) we get phase and lag matched signals $$v_i(n) = \Re\left\{ u_{f,x_i}^a(n - \tau_d^{i,j}) \cdot e^{i \cdot \varphi_{\tau_d}^{i,j}} \right\}, \quad v_j(n) = \Re\left\{ u_{g,x_j}^a(n) \right\}.$$

When choosing functions as $f: x_i \mapsto A_i$ and $g: x_j \mapsto A_j$ the Amplitude to Amplitude Coupling (AAC) features for a cross-correlation matrix $$C_{AAC}(X_i^n, X_j^n) = \begin{pmatrix} c_{max}^{1,1} & \cdots & c_{max}^{1,j} \\ \vdots & \ddots & \vdots \\ c_{max}^{i,1} & \cdots & c_{max}^{i,j} \end{pmatrix}.$$

Also, the matched signals can readily be used to produce the other feature matrices, for example using the modulation index (MI) to generate $$MI_{AAC}(X_i^n, X_j^n) = \begin{pmatrix} MI_{c_{max}}^{1,1} & \cdots & MI_{c_{max}}^{1,j} \\ \vdots & \ddots & \vdots \\ MI_{c_{max}}^{i,1} & \cdots & MI_{c_{max}}^{i,j} \end{pmatrix},$$

and the heights ratio (HR) for matrix $$HR_{AAC}(X_i^n, X_j^n) = \begin{pmatrix} HR_{c_{max}}^{1,1} & \cdots & HR_{c_{max}}^{1,j} \\ \vdots & \ddots & \vdots \\ HR_{c_{max}}^{i,1} & \cdots & HR_{c_{max}}^{i,j} \end{pmatrix},$$

where $MI_{c_{max}}^{i,j} = MI(P, U)|P(k) = m_k(v_i(n), v_j(n))$ and $HR_{c_{max}}^{i,j} = HR(P)|P(k) = m_k(v_i(n), v_j(n))$.

Similarly, when assigning $f: x_i \mapsto \varphi_i$, $g: x_j \mapsto A_j$ we get Phase to Amplitude Coupling (PAC) features $C_{PAC}$, $MI_{PAC}$ and $HR_{PAC}$. And when $f: x_i \mapsto n \cdot \varphi_i$, $g: x_j \mapsto m \cdot \varphi_j$ the Phase to Phase Coupling (PPC) features are $C_{PPC}$, $MI_{PPC}$ and $HR_{PPC}$. Any other feature measures can be collected similarly into a feature matrix format such as PLV using the PPC setting is then, for example, $$PLV_{PPC}(X_i^n, X_j^n) = \begin{pmatrix} PLV^{1,1} & \cdots & PLV^{1,j} \\ \vdots & \ddots & \vdots \\ PLV^{i,1} & \cdots & PLV^{i,j} \end{pmatrix}.$$

Resulting features of coupling, causality etc. may be used with statistical inference and artificial intelligence approaches to generate learning structures used in generating estimates, likelihoods, and/or predictions of current and/or future neurological functions. Such structures may be based on probability distributions of feature sequences (e.g. vectors or matrices) for example with bootstrapping and significance estimation or kernel density estimation. Dimensionality reduction and/or feature transformations may be applied for the features, such as PCA, manifold learning (e.g. geodesic distance methods, such as Isomap), or BSS (Blind Source Separation) methods, such as ICA. Feature search and/or selection methods may be used, such as sequential search or genetic algorithms, to optimize and increase the performance of the learning structure. Regression methods, e.g. GLM, may be applied for feature sequences. A segmentation and/or detection of sequences may be used to process feature sequences, e.g. with distance metrics and thresholds, or applying a model change detection method, e.g. based on the Bayesian Information Criterion (BIC), to direct learning into relevant signal areas and/or process data for learning. Classifier-based learning structures may be used. The classifiers structures may be based on distance measures and thresholds, or probability distribution differences, such as a Bayesian classifier or a GMM. A dynamic structure may be used, such as a HMM. Kernel based classifiers may be used, such as SVMs, or nonparametric classifiers, such as kNN. A neural network may be applied as the learning structure with optimization using e.g. backpropagation. The neural network may be a deep learning architecture, such as a Deep Belief Network (DBN), a Convolutional Neural Network (CNN), or a Recurrent Neural Network (RNN) that implicitly, or explicitly contain also any feature selection, transformation, segmentation, and/or classification capabilities. A deep learning architecture may be constructed containing Short Long Term Memory (SLTM) blocks. The deep architecture neural network may be constructed as a residual neural network.

Learning structures may be applied to provide new automated Artificial Intelligence (AI) EEG signal monitoring solutions and to enable advanced AI patient status estimation and diagnostics capabilities such as EEG signal model identification (e.g. burst suppression pattern detection and monitoring), artefact detection and filtering (e.g. eye movements, muscle artefacts, or sensor failures/decoupling), correct/incorrect operation mode detection (e.g. seizure detection, sleep phase estimation), neurological function classification (e.g. normality estimation, dysfunction type (delirium, seizure, etc.), neural damage type (diffuse injury/ neurotrauma)). Also, pharmacological compound effect modeling/tracking may be achieved (e.g. depth of anesthesia, long term drug therapy intervention monitoring/control (therapeutic drug infusion monitoring/control)).

Learning structures and resulting AI solutions may be used in prediction and monitoring tasks such as Injury/ dysfunction recovery estimation and control (e.g. estimate of therapeutic intervention efficacy with drug, transcranial Electric Stimulation (tES), or Transcranial Magnetic Stimulation (TMS) treatment control), or likelihood of future status changes and/or additional injury/dysfunction (e.g. seizures, delirium, or death).

Automated AI EEG solution based on learning structures may be used to provide long term continuous neurological status monitoring to ICUs providing a translation of the complex EEG signal information into a much more user accessible form of specific indexes, status indications, and notifications. AI based EEG analysis may be applied with other brain imaging (functional and/or topographic, such as Magnetoencephalography (MEG), (functional) Magnetic Resonance Imaging ((f)MRI), or Positron Emission Tomography (PET) imaging) to provide image modality fusion mappings, for example, for surgery planning purposes. AI EEG may be used in sleep monitoring, e.g. quality and quantity of sleep estimations, or in various other nonmedical tasks such as in brain interfaces (e.g. user interfaces, affective/cognitive/context state evaluation).

Furthermore, AI EEG may be applied in research and development of new therapy such as new tES and TMS stimulation device (e.g. transcranial Direct Current Stimulation (tDCS), Alternating Current (tACS), Pulsed Current (tPCS), Random Noise (tRNS), or Rippled Current (tRCS)), new drug development, or drug neurological effect evaluation. In basic scientific research, AI EEG neurological function evaluation may be used, e.g. as a cognitive neuroimaging method in cognitive research settings.

As already explained earlier, the data processing unit 100 may comprise at least one processor 200 and at least one memory 202. In an embodiment, the one or more memories 202 and the computer program code with the one or more processors 200 may cause the apparatus to form of the coupling information between the at least two of the EEG signals. The one or more memories 202 and the computer program code with the one or more processors 200 may also cause the apparatus to normalize the first information and form the first comparison between the phase coupling information and the corresponding first template information based on the reference brain function.

In an embodiment, the one or more memories 202 and the computer program code with the one or more processors 200 may cause the apparatus to form of the second information about power of the two EEG signals. The one or more memories 202 and the computer program code with the one or more processors 200 may also cause the apparatus to form the second comparison between the second information and the corresponding power template information that is based on a reference brain function. Finally, the one or more memories 202 and the computer program code with the one or more processors 200 may cause the apparatus to output the information about the second comparison.

In an embodiment, the one or more memories 202 and the computer program code with the one or more processors 200 may cause the apparatus to combine of the first information and the second information, and to output the information about the combined comparison.

The advanced brain function measures may also prove to be useful in similar application cases such as sleep monitoring or measurement of neural therapy effectiveness. It is clear, that machine learning and AI (Artificial Intelligence) in general is the cornerstone for brain signal analysis for a plurality of future applications in medicine, brain user interfaces, cognitive sciences, and affective computing.

The deviation from normal brain function measured by the comparison between the EEG data and corresponding data of a reference brain function may be due to brain dysfunction. Brain dysfunction may occur due to hypoxic-ischemic encephalopathy/brain injury, traumatic brain injury, stroke, intracerebral or subarachnoid hemorrhage or other cerebral bleed, septic encephalopathy, meningitis, encephalitis, vasculitis, hepatic encephalopathy, toxic or metabolic derangements, or as side effects of medications. Brain dysfunction may manifest itself in the form of coma or delirium, for example. Furthermore, brain dysfunction may occur due to, for example, neurodegenerative diseases such as Alzheimer's or Parkinson's disease, vascular, frontotemporal or Lewy bodies dementia, multiple sclerosis, mental conditions including depressive, bipolar and schizophrenic disorders, epilepsy, migraine, attention deficit disorder, or attention deficit hyperactivity disorder.

The slow waves are seen during general anesthesia but also during natural sleep. Single slow waves, i.e. K-complexes, are seen in non-REM (NREM) sleep stage 2 and continuous slow wave activity during deep NREM sleep (stages 3). The phase-to-phase, phase-to-amplitude and/or amplitude-to-phase coupling(s) of slow waves between at least two electroencephalographic signals can be measured during natural sleep and a comparison to a corresponding phase coupling template information that is based on a reference brain function can be made. The reference brain function may represent healthy individual or an individual with a specific brain dysfunction. Furthermore, the reference brain function may represent a measurement during sleep or while being awake. The comparison can be used, for example, to detect and/or measure the amount of slow wave activity, different sleep stages, epileptic activity, or brain dysfunction/injury.

Slow waves are seen sometimes also during epileptic activity/seizures or brain dysfunction/injury. On the other hand, normal slow wave activity seen during natural sleep and anesthesia may be absent or disturbed during epileptic activity/seizures or brain dysfunction/injury. The phase-to-phase, phase-to-amplitude and/or amplitude-to-phase coupling(s) of slow waves between at least two electroencephalographic signals can be measured during epileptic activity/seizures or brain dysfunction/injury and a comparison with a corresponding phase coupling template information that is based on a reference brain function can be made. The reference brain function may represent healthy individual or an individual with epileptic activity/seizures or specific brain dysfunction. Furthermore, the reference brain function may represent the same or other individual. Furthermore, the reference brain function may represent a measurement during natural sleep, anesthesia or while being awake. The comparison can be used, for example, to detect and/or measure the amount of epileptic activity/seizures or brain dysfunction/injury.

Slow waves are seen at different levels of general anesthesia. While continuous slow wave activity can be seen in deep sedation after loss of consciousness, the activity is also seen in very deep anesthesia where burst suppression pattern is seen in the EEG. This state is also sometimes referred as medical coma. The phase coupling pattern of slow waves may differ substantially between the state in which continuous slow wave activity is seen and the state in which burst suppression pattern is seen. The phase-to-phase, phase-to-amplitude and/or amplitude-to-phase coupling(s) of slow waves between at least two electroencephalographic signals can be measured at different levels of anesthesia and a comparison to a corresponding phase coupling template information that is based on a reference brain function can be made. The reference brain function may represent healthy individual or an individual with a specific brain dysfunction/injury. Furthermore, the reference brain function may represent different levels of anesthesia such as awake state, light sedation, deep sedation during which continuous slow wave activity is seen, or burst suppression pattern. The comparison can be used, for example, to detect and/or measure the level or the depth of anesthesia, burst suppression pattern, or brain dysfunction/injury.

Figure 12:
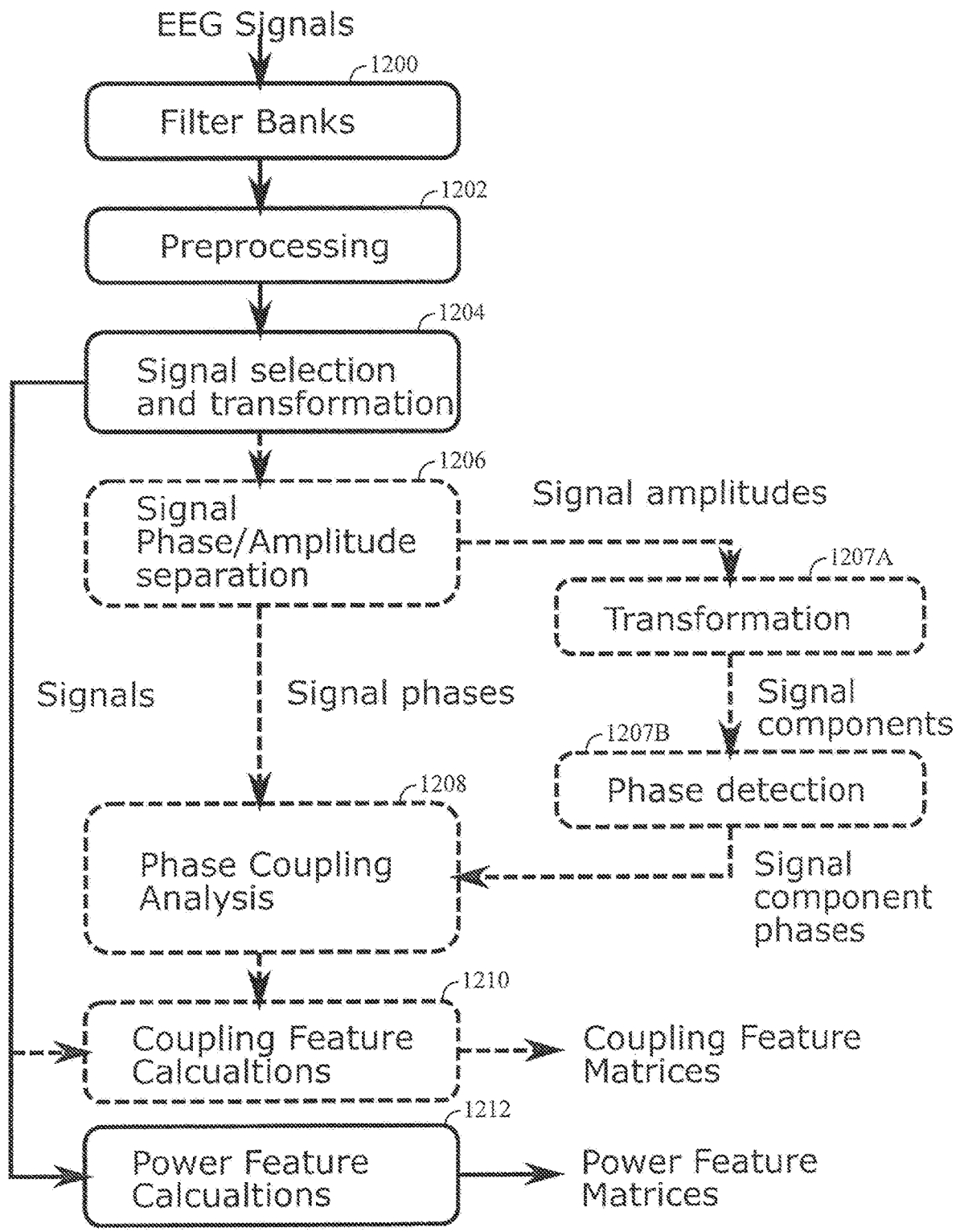
FIG. 12 illustrates an example of a flow chart of the phase coupling and power measurements.

FIG. 12 presents an example of a flow chart of the method related to signal coupling determination with respect to the slow waves. In step 1200, the EEG signals may be filtered in filter banks. This step may be included in the detection. In step 1202, desired EEG signals may be preprocessed which may refer to filtering out noise and artefacts, detecting electrodes having poor contacts and potentially removing their signals from further processing, for example.

In step 1204, desired EEG signals may be selected and potentially transformed for the measurement. This step may also be included in the detection. In this step 1202, the one or more EEG signals may also be transformed. In step 1206, the phase and amplitude information of the one or more EEG signals are separated from each other. In step 1208, the phase-to-phase, phase-to-amplitude and/or amplitude-to-phase coupling is determined and/or analysed. In an embodiment, the amplitudes of the EEG signals are transformed into signal components in step 1207A between steps 1206 and 1208. Then in this embodiment, phase information of the amplitudes (envelope) is detected in step 1207B. The detected phase information of the amplitudes (envelope) may be used in the phase-to-amplitude and/or amplitude-to-phase coupling determination in step 1208. In step 1210, coupling feature (strength, time lag, phase, direction or the like of coupling) calculations may be performed, which may provide one or more coupling feature matrices, which may also include information about the EEG signal power (see FIGS. 4 to 6, and 8 to 11). In step 1212, power feature calculation (second information about power of at least one electroencephalographic signal) may be performed which may provide power feature matrices (see FIGS. 7 and 9).

Figure 13:
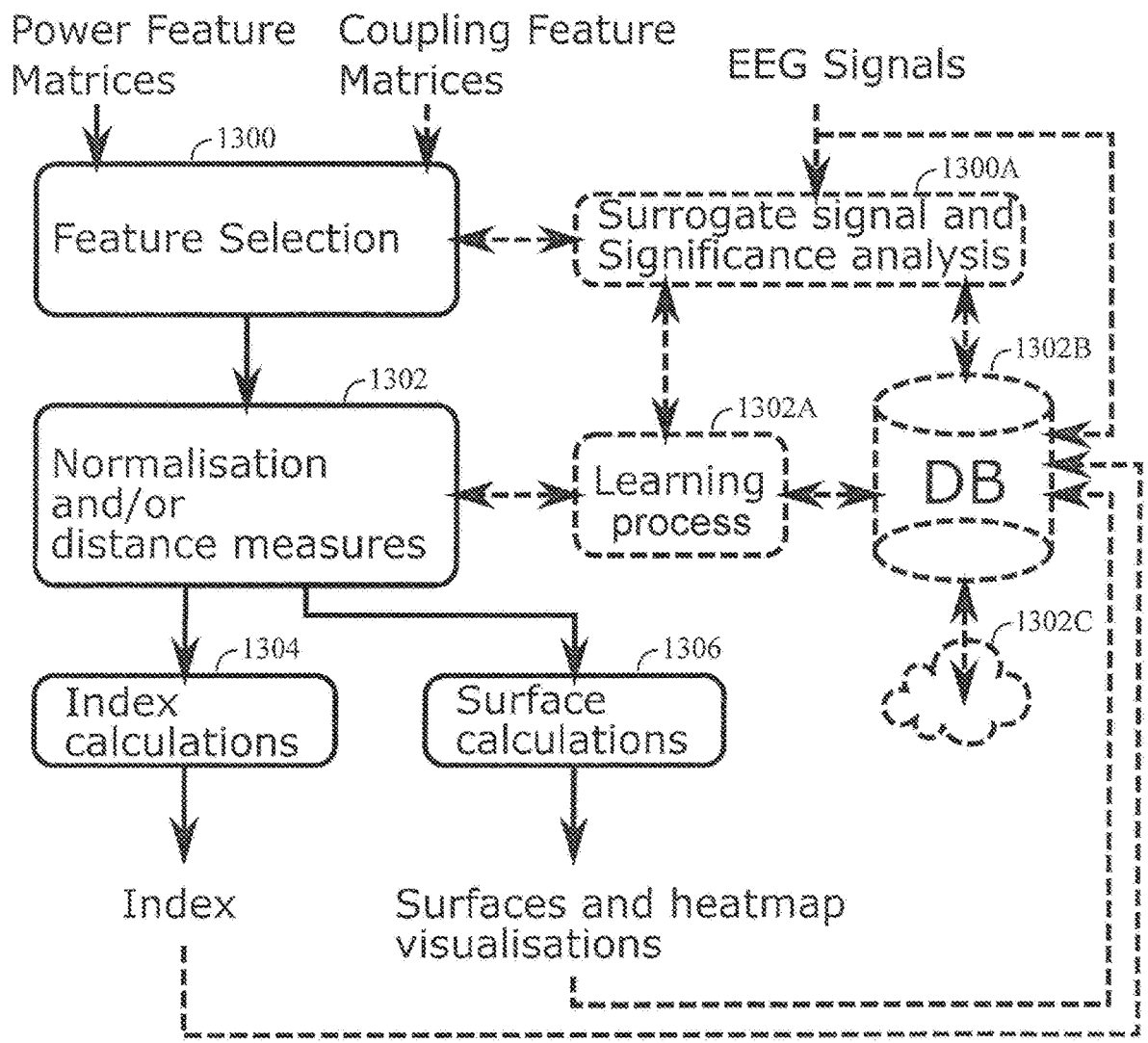
FIG. 13 illustrates an example of a flow chart of calculations of coupling feature indices, visualization and learning.

FIG. 13 presents an example of a flow chart of the coupling feature index calculations, visualization and learning (see FIG. 11) with respect to the slow waves. In step 1300, the power feature matrices and the coupling feature matrices are received by a feature selection step 1300. The feature selection step 1300 may select either or both the power feature matrices and the coupling feature matrices for the next step. The feature selection step 1300 may also receive information about surrogate and significance analysis step 1300A. Additionally or alternatively, the feature selection step 1300 may provide information about feature selection to the surrogate and significance analysis step 1300A. In step 1302, the selected one or more feature matrices may be normalized and/or compared with the corresponding matrices of the reference brain functions (reference brain function (healthy brain) and second reference brain function (not-healthy brain)) in order to form distance measures of the features. The step 1302 may input information to or receive information from a learning process 1302A which may be performed using at least one processor and at least one memory that includes a suitable computer program. The learning process 1302A may communicate with a data base 1302B which, in turn, may have an operational connection, wired or wireless, with a cloud server 1302C. The data base 1302B and/or the cloud server 1302C may be used as a data storage of the raw EEG signals and the processed EEG signals. Additionally or alternatively, the data base 1302B and/or the cloud server 1302C may process the EEG signals in one or more ways according to the prior art and/or according the what is taught in this description. In step 1304, one or more indices are formed of the normalized and/or distance measures provided by the step 1302. The one or more indices may be stored or used in the processes in the data base 1302B and/or the cloud server 1302C. In step 1306, surface computation may be performed and results as shown in FIGS. 3 to 6 and 8 may be provided.

Figure 14:
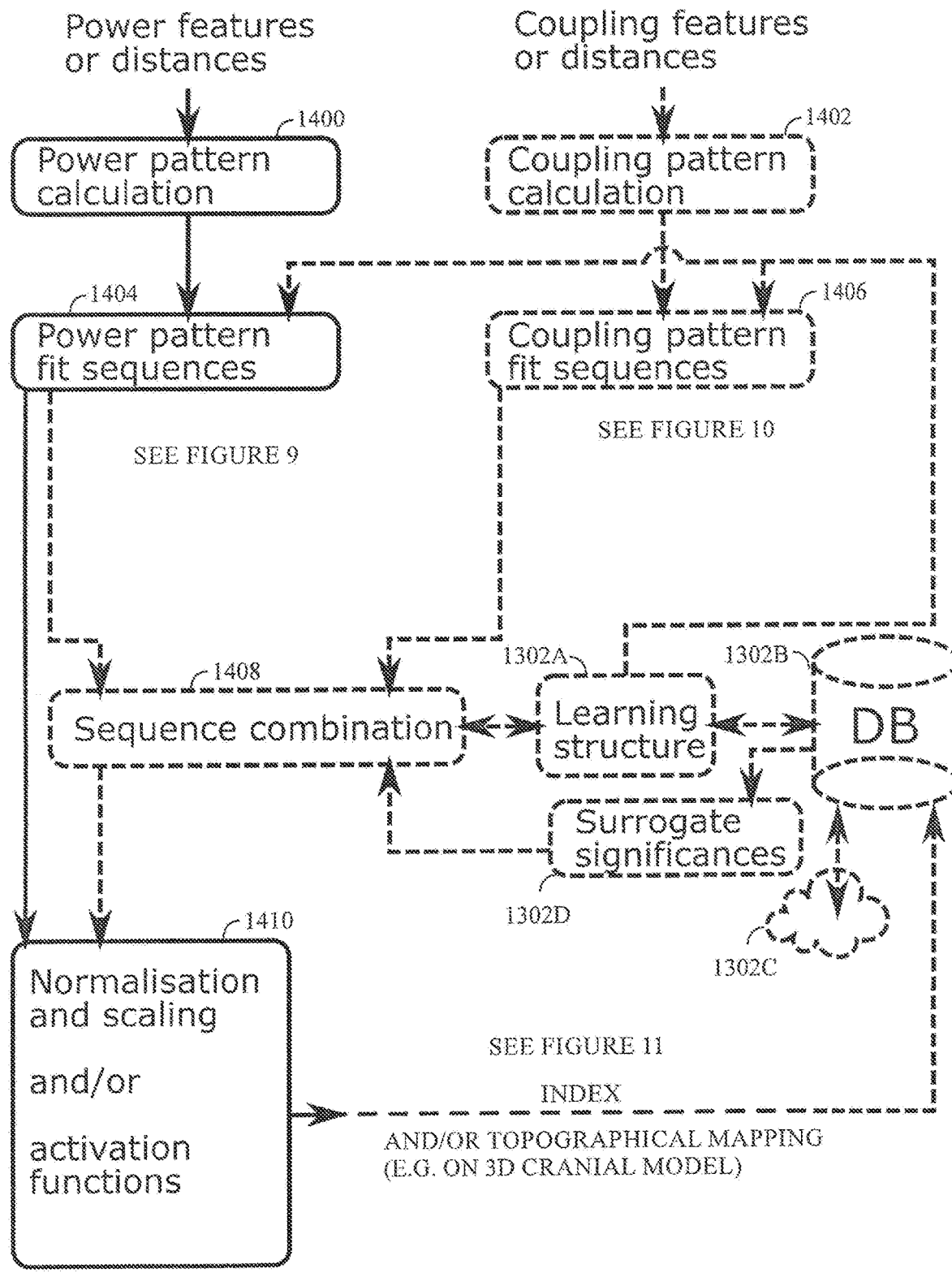
FIG. 14 illustrates an example of a flow chart of index calculation.

FIG. 14 presents an example of how the coupling indices may be calculated (see FIGS. 13 and 11). The step 1400 may receive the power features and/or distances formed in step 1302 of FIG. 13. The power features and/or distances may come from the step 1302, the data bank 1302B or the cloud server 1302C. The step 1400 may then perform power pattern calculations. The step 1404 may form power pattern fit sequences from the power pattern calculations similar to those in FIG. 9. The step 1402, in turn, may receive coupling features and/or distances from step 1206 of FIG. 12 and may form the coupling pattern. The step 1406 may then forms coupling pattern fit sequences from the coupling pattern calculations provided by step 1402.

The step 1408 may receive the power pattern fit sequences and a coupling pattern fit sequences similar to that shown in FIG. 10 and formed in step 1208 of FIG. 12. The power pattern fit sequences and the coupling pattern fit sequences may be combined in step 1408 for forming the index or indices similar to that shown in FIG. 11. The index or indices may be formed according to step 1304 shown in FIG. 13. Additionally the combined pattern may be normalized, scaled and processed with at least one activation function of the step 1410. The activation function may be a non-linear function which scales the values of the combined pattern on a desired range. The function may be such as a transfer function or a membership function and it is known in the fields of artificial neural networks and fuzzy logic. The learning process 1302A may communicate with the sequence combination step 1408 such that the information may be exchanged in both directions. In similar manner to FIG. 13, the data bank 1302B and the cloud server 1302C may store and/or process the information of the EEG signals they receive and/or include. Surrogate significances may be retrieved from the date base 1302B and fed to the sequence combination 1408. Alternatively or additionally, a topographical mapping may be formed in the step 1410. The topographical mapping may be placed on a 3-dimensional cranial model, for example.

In an embodiment, the apparatus for brain function measurement may comprise or be connected with an administration device 104 (see FIG. 1). The administration device 104 may include or be an infusion pump, for example. In an embodiment, the apparatus for brain function measurement may comprise or be connected with a blood measuring device 106. The blood measuring device 106 may comprise a sampling device which is configured to take a blood sample i.e. a certain amount of blood from the person 108. The sampling device may comprise a vacutainer and/or a hypodermic needle. Additionally, the blood measuring device 106 may comprise a blood analysing device which may perform a chemical or optical analysis of the blood, for example.

FIG. 1 also illustrates a stimulator 112 which is optional and may be used in an embodiment.

The presence of anesthetic compounds, normally seen as hindering any traditional EEG analysis or neurological assessments, can reveal fundamental aspects of the brain function to be used in automatic signal analysis approaches of the brain function to produce brain function related measures and estimates. Advanced signal analysis methods and brain function modeling are again required to produce such refined measures. The advanced brain function measures may also prove to be useful in similar application cases such as measurement of neural therapy effectiveness to relieve or cure a dysfunction of the brain. The machine learning and AI in general may also be used for brain signal analysis during presence of anesthetic compounds.

The phase-to-phase coupling between at least two electroencephalographic signals, phase-to-amplitude coupling between at least two electroencephalographic signals and amplitude-to-phase coupling between at least two electroencephalographic signals may be assessed during anesthesia and between different anesthetic levels. The level of anesthesia may be controlled with the administration device 104 such as an infusion pump may infuse the anesthetic drug substance, which is in a fluidal form, into the body of the person 110. In this manner, the person 110 is exposed to varying amounts of anesthetic drug substance in a controlled manner. The anesthetic drug substance comprises one anesthetic drug or a combination of anesthetic drugs. The anesthetic drug substance may be propofol, for example. The anesthetic drug substance may be infused into at least one vein of a circulatory system of the person. The anesthetic drug substance may be infused continuously or may be introduced as one or more boluses. The anesthetic drug substance may then be called an intravenous drug substance. Additionally or alternatively arterial, epidural and/or subcutaneous, intrathecal and muscular infusion may be used. Infusion in this context also includes injection. The infusion pumps can administer anesthetic drug substances very accurately. Manual injections of the anesthetic drug substance are more inaccurate and expensive. Infusion pumps can be used to administer the anesthetic drug substance adaptively such that the input varies with respect to a desired parameter such as time, the EEG measurement and the measured concentration of the anesthetic drug substance, for example.

Additionally or alternatively, an inhalation device as the administration device 104 may be used for inhaling the anesthetic drug substance through a mouth piece. The inhalation may be continuous or the anesthetic drug substance may be introduced in a step-wise manner, each step increasing or decreasing the dose.

The data processing unit 100 may receive the EEG data based on the EEG measurement of the brain of the person 110 while the person 110 is exposed to one or more estimated or measured non-zero amounts of anesthetic drug substance.

The at least one anesthetic drug substance may have one or more estimated or measured non-zero levels of concentration in the body 108 of the person 110 as a function of time. It is possible to measure the EEG in only one non-zero concentration which may be either estimated or measured. Instead of one level of concentration, the anesthetic drug substance may have a plurality of concentration levels as a function of time. The at least one concentration level may be estimated or measured. The EEG effect of the anesthetic drug substance typically depends on its concentration level in the body 108. The EEG characteristics such as burst suppression pattern may be used for determining the effect or level of the anesthetic drug. The EEG characteristics such as a burst suppression pattern may be used to determine the amount of administration of the anesthetic drug substance. Alternatively or in addition, the EEG characteristic used may include a feature, such as slow wave activity, which is caused by the administration of the drug, and for example the maximal effect of the drug on this feature is utilized. Still alternatively or in addition, the used EEG characteristic may include determination of a change in the feature crossing a predetermined threshold in the range of the slow wave activity, which is caused by the administration of the drug. The predetermined threshold may be based on experience of a person skilled in the art. The predetermined threshold may be based on simulation. The predetermined threshold may be based on the expected effect of the drug, the effect and use being published in the literature. Because the effect of the drug varies as a function of time a person skilled in the art knows when the predetermined threshold is crossed on the basis of his/her knowledge. The slow wave activity may be measured on the basis of the phase-to-phase, phase-to-amplitude and/or amplitude-to-phase coupling explained earlier in the description. Additionally, the slow wave activity may be measured on the basis of the power measurements of the EEG as also explained earlier in the description.

The administration of the at least one anesthetic drug substance may improve the measurement of the phase coupling (phase-to-phase, phase-to-amplitude and/or amplitude-to-phase coupling). The administration of the at least one anesthetic drug substance may increase the signal-to-noise ratio by, for example, lowering other brain activity and increase slow wave activity.

The phase-to-phase coupling between at least two electroencephalographic signals, phase-to-amplitude coupling between at least two electroencephalographic signals and amplitude-to-phase coupling between at least two electroencephalographic signals may be assessed during stimulation and compared between the state in which stimulation is applied and is not applied. The stimulation may improve the detection of existing or non-existing coupling by, for example, increasing slow wave activity and reducing other brain activity.

Figure 15:
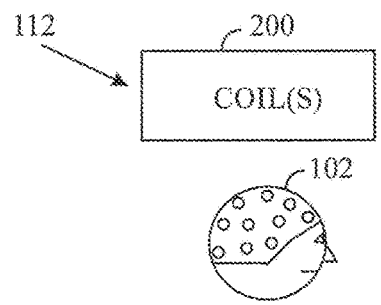
FIG. 15 illustrates an example of a magnetic stimulator.

In an embodiment an example of which is illustrated in FIG. 15, the stimulator 112 may comprise at least one a coil 200 for providing the brain with magnetic stimulation. The stimulation may be performed transcranially so that the coil or the coils are placed outside the head in the proximity of the area stimulated. When alternating electric current is fed to the coil 200, an alternating magnetic field is generated. The stimulation may be performed in a repeated manner so that magnetic stimulation pulses are given repeatedly in a specific frequency. The frequency may be for example approximately 0.8 Hz or 5 Hz and the stimulation may be continued for example for about 30 minutes. The stimulation may be given to a specific location on the scalp such as the area over the sensorimotor cortex to stimulate a specific area of the cortex. The stimulation intensity may be for example 65-85% of maximal stimulator output corresponding to maximal electric field of 150-180 V/m.

Figure 16:
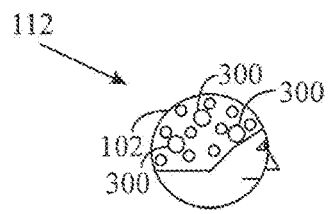
FIG. 16 illustrates an example of an electric stimulator.

In an embodiment an example of which is illustrated in FIG. 16, the stimulator 112 may comprise at least one stimulating electrode 300 for providing the brain with electric stimulation. The at least one stimulating electrode 300 may be included in the electrode system 102 or separate from the electrode system 102. The electrode 300 may transmit electromagnetic radiation wirelessly or feed alternating or direct electric current to the brain through the galvanic contact with the brain. The stimulation may be performed transcranially so that the electrode or the electrodes are placed on the scalp in the proximity of the area stimulated. The stimulation may be given in an oscillatory manner so that the amplitude of the direct current of the direction of the alternating current is changed in a specific frequency. The frequency may be for example approximately 0.8 Hz or 5 Hz and the stimulation may be continued for example for about 30 minutes. The stimulation may be given to a specific location on the scalp such as the area over the frontal cortex to stimulate a specific area of the cortex. With direct current stimulation, the anodal electrode (the electrode with positive polarity) may be located over the frontal cortex and the cathodal electrode (the electrode with negative polarity) may serve as a reference electrode and may be placed on the deltoid muscle. The stimulation current may vary for example between 0 and 0.6 mA and the maximum current density could be approximately 0.5 mAcm-2.

Alternatively or in addition to the stimulation on the scalp, the electrical stimulation may be applied directly to the brain tissue by placing the electrodes on the surface of the cortex or inside the brain tissue in which case the approach is called deep brain stimulation.

Figure 17:
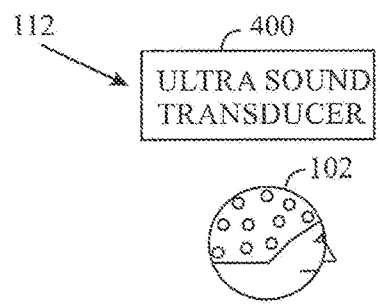
FIG. 17 illustrates an example of an ultrasound stimulator.

In an embodiment an example of which is illustrated in FIG. 17, the stimulator 112 may comprise at least one an ultrasound transducer 400 for providing the brain with acoustic stimulation. The ultrasound transducer 400 may direct ultrasound to the whole brain or a section of the brain.

In an embodiment an example of which is similar to those illustrated in FIGS. 15 to 17, the stimulator 112 may comprise at least one optical fiber or at least one source of optical radiation for providing the brain with optical stimulation. The source of optical radiation may comprise at least one LED (Light Emitting Diode) or at least one laser, for example. The at least one optical fiber or the at least one source of optical radiation may direct the optical stimulation to the whole brain, a section of the brain or several sections of the brain. In optical stimulation, an optogenetic approach may be combined. In this approach, the neurons have been made sensitive to optical stimulation by genetic modification.

Figure 18:
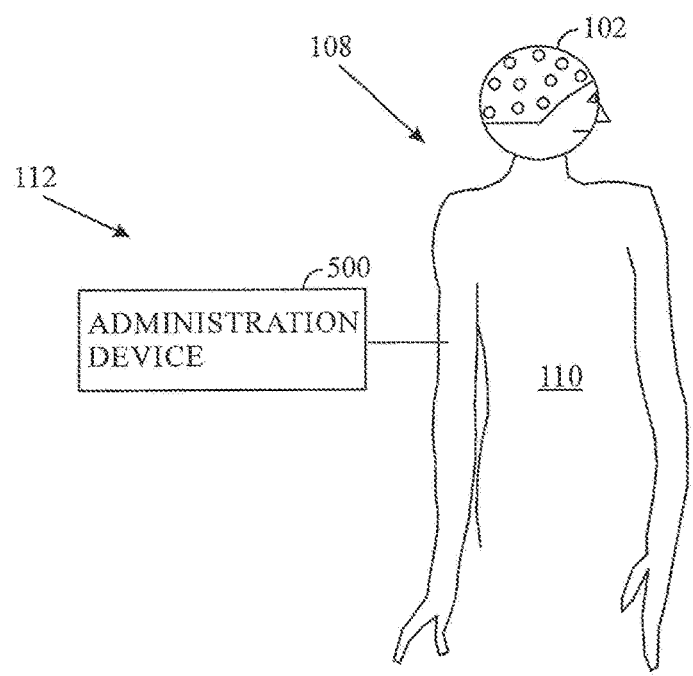
FIG. 18 illustrates an example of an administration device for chemical stimulation.

In an embodiment an example of which is illustrated in FIG. 18, the stimulator 112 may comprise at least one stimulating administration device 500 for providing the brain with chemical stimulation. The stimulating administration device 500 may comprise an infusion pump and/or an inhalation device similar to the administration device 104. The stimulating administration device 500 may provide the person 110 with at least one stimulating drug. A stimulating drug here means a drug which may induce a missing activity or reduce an abnormal activity. For example, the stimulating drugs for slow wave activity could be intravenous GABAergic anesthetics, inhalational GABAergic anesthetics, opioids and/or alpha2-adrenergic anesthetics. The group of the other intravenous GABAergic anesthetics may include etomidate, thiopental, and/or methohexital, for example. The group of the inhalational GABAergic anesthetics may include isoflurane, desflurane, and/or sevoflurane, for example. The group of the opioids may include morphine, fentanyl, alfentanil, remifentanil, and/or sufentanil, for example. The group of the alpha2-adrenergic anesthetics may include dexmedetomidine or the like, for example.

In an embodiment, the stimulation may be used on the basis of the first information. In an embodiment, the stimulation may be used to improve the brain function of a person with determined abnormal brain activity. In an embodiment, the stimulation may be used to accelerate the improvement towards the normal brain activity when an abnormal activity in the brain has been determined on the basis of the first information. In an embodiment, the stimulation may be used to reach a brain activity that is closer to the normal brain activity than that without the stimulation when an abnormal activity in the brain has been determined on the basis of the first information. In an embodiment, the stimulation may be applied to persons with the estimated good outcome on the basis of the first information because the stimulation may help them in the curing process. In an embodiment, the stimulation may be applied to persons with the estimated poor outcome on the basis of the first information because the stimulation may help them to cure. In addition to the first information also the second information may be used in these cases.

Figure 19:
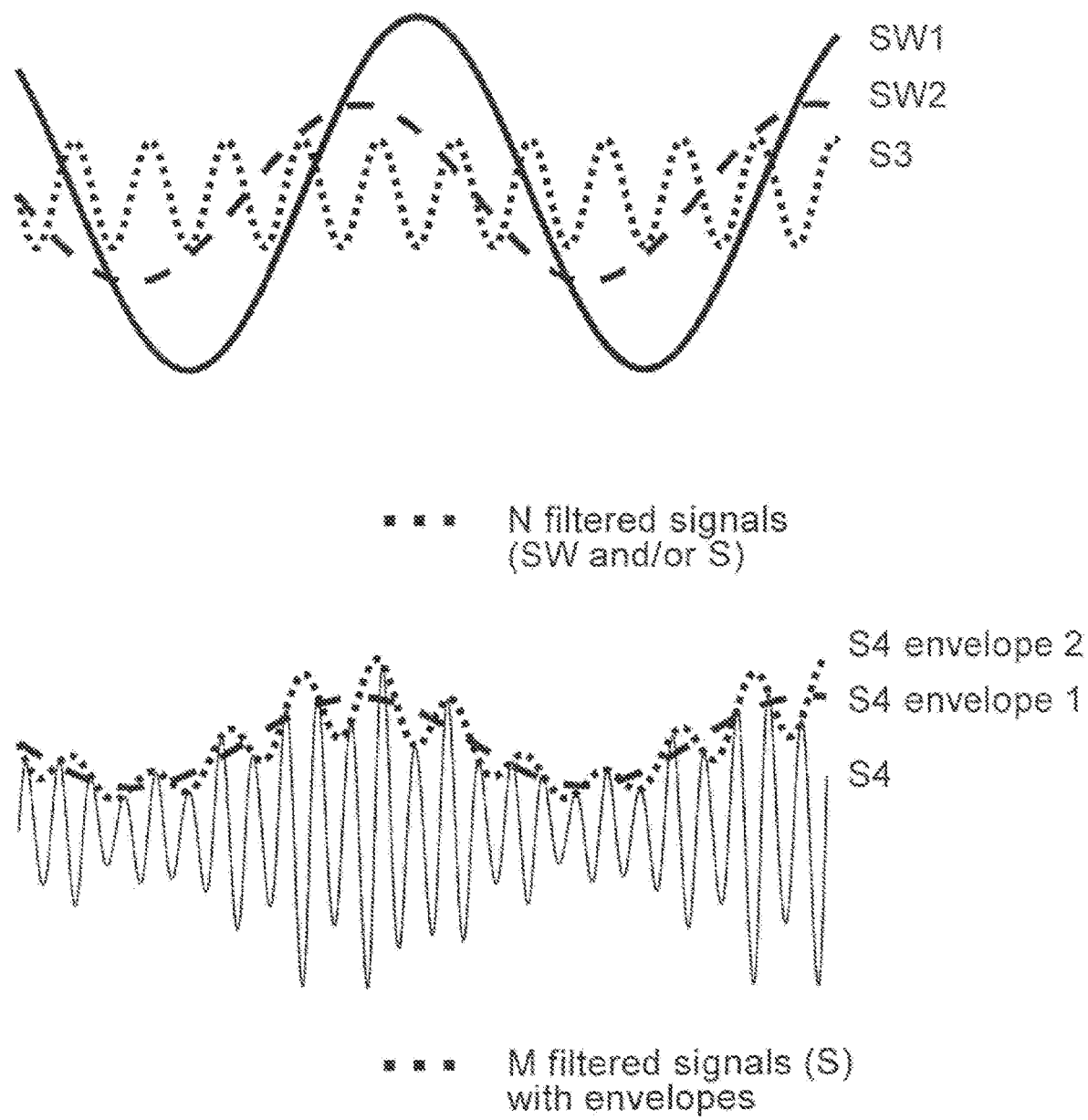
FIG. 19 illustrates an example of phase-to-amplitude coupling.

FIG. 19 illustrates an example of phase-to-amplitude coupling. The number of EEG signals, which are received or selected for the measurement, may be N, where N is at least two, and they may be filtered at first. There may be M EEG signal which are also received or selected for the measurement, M being smaller than N. Then one or more slow-wave signals (SW1 and SW2) and upto K signals (S3, S4 envelope 1 and S4 envelope 2) may be compared, where K is an integer larger than zero. That is, of the K signals their signal components such as amplitudes may be compared with the phases of the slow-wave signals. The amplitudes of the K signals refer to envelopes of the K signals. The variation of the amplitudes/envelopes being in the slow-wave frequency band. In this example, the amplitude S4 envelope 1 is a slow wave and can be taken into account in the coupling. The amplitude S4 envelope 2, in turn, is not in the slow-wave band and has no contribution in the slow-wave coupling (although there may be a coupling between the signals S3 and S4 which, per se, are not in the slow-wave band).

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus comprising:
one or more processors, and
one or more memories including computer program code;
    wherein the one or more memories and the computer program code with the one or more processors are configured to cause the apparatus at least to:
receive at least two electroencephalographic signals of a brain of a person;
form first information by measuring phase-to-phase coupling between at least two electroencephalographic signals;
form second information by measuring power of at least one electroencephalographic signal, the first and second information being related to slow waves having frequencies at or lower than 1 Hz;
combine the first and second information;
form an index based on the combined first and second information on the basis of feature or distance calculations; and
predict a further development of neurological function level of the brain of the person towards a good outcome provided that a difference between the first information and coupling template information is smaller than a first determined threshold and at least one of the following: a power level of the second information is higher than a second determined threshold, and a difference between the second information and corresponding power template information is smaller than a third determined threshold.

2. The apparatus of claim 1, wherein the one or more memories and computer program code with the one or more processors are configured to cause the apparatus to perform a combined comparison between the combined information and corresponding combined template information that is based on a reference brain function, and output information about the combined comparison.

3. The apparatus of claim 1, wherein the one or more memories and computer program code with the one or more processors are configured to cause the apparatus to receive the at least two electroencephalographic signals of the brain of the person who is at least expected to be under influence of at least one in the following list: epileptic activity, brain dysfunction, neural injury, sleep, and one or more non-zero amounts of anesthetic drug substance.

4. The apparatus of claim 1, wherein the one or more memories and computer program code with the one or more processors are configured to cause the apparatus to separate phase and amplitude of the at least two electroencephalographic signals based on a phase separating convolution transform.

5. The apparatus of claim 1, wherein the one or more memories and computer program code with the one or more processors are configured to cause the apparatus to form the first information based on at least one of the following: information theoretical measures, phase locking multipliers, demodulation, probability density estimation, bivariate measures, correlation, multivariate causality measures, and coupling fingerprints.

6. The apparatus of claim 1, wherein the apparatus comprises an electrode system configured to provide the at least two electroencephalographic signals of the brain of the person.

7. The apparatus of claim 1, wherein the one or more memories and the computer program code with the one or more processors are configured to cause the apparatus to normalize the first and second information.

8. The apparatus of claim 1, wherein the prediction is based on a machine-learned structure.

9. The apparatus of claim 8, the prediction is used in providing and/or proposing to provide injury/dysfunction recovery estimation and control.

10. The apparatus of claim 1, the prediction is used in providing and/or proposing to provide injury/dysfunction recovery estimation and control.

11. An apparatus comprising one or more processors, and one or more memories including computer program code, wherein the one or more memories and the computer program code with the one or more processors are configured to cause the apparatus at least to:
receive at least two electroencephalographic signals of a brain of a person;
form first information by measuring phase-to-phase coupling between at least two electroencephalographic signals;
form second information by measuring power of at least one electroencephalographic signal, the first and second information being related to slow waves having frequencies at or lower than 1 Hz;
perform a first comparison between the first information and corresponding coupling template information that is based on a reference brain function;
perform a second comparison between the second information and corresponding power template information that is based on a reference brain function;
combine the first and second comparison;
form an index based on the combined first and second comparison on the basis of feature or distance calculations; and
predict a further development of neurological function level of the brain of the person towards a good outcome provided that a difference between the first information and coupling template information is smaller than a first determined threshold and at least one of the following: a power level of the second information is higher than a second determined threshold, and a difference between the second information and corresponding power template information is smaller than a third determined threshold.

12. The apparatus of claim 11, wherein the one or more memories and computer program code with the one or more processors are configured to cause the apparatus to perform the second comparison between the second information and corresponding power template information that is based on a reference brain function in order to normalize the second information.

13. The apparatus of claim 11, wherein the one or more memories and computer program code with the one or more processors are configured to cause the apparatus to:
cause the apparatus to receive the at least two electroencephalographic signals of the brain of the person who is at least expected to be under influence of at least one in the following list: epileptic activity, brain dysfunction, neural injury, sleep, and one or more non-zero amounts of anesthetic drug substance; and
estimate whether the person is under the influence of the at least one in the list based on the first comparison, and present a result of the estimation.

14. The apparatus of claim 11, wherein the one or more memories and computer program code with the one or more processors are configured to cause the apparatus to predict a neurological function level of the person based on the first comparison.

15. The apparatus of claim 14, wherein the one or more memories and computer program code with the one or more processors are configured to cause the apparatus to predict a further development of the neurological function level of the person towards a poor outcome if a difference between the first information and the coupling template information is larger than a fourth determined threshold and corresponding power template information is larger than a fifth determined threshold.

16. The apparatus of claim 14, wherein the one or more memories and computer program code with the one or more processors are configured to cause the apparatus to predict a further development of the neurological function level of the person towards a poor outcome if a difference between the first information and the coupling template information is larger than a fourth determined threshold and the power level of the second information is lower than a fifth determined threshold.

17. A method performed in connection with at least one hardware processor and an electrode sensor system, the method comprising:
receiving a plurality of electroencephalographic signals of a brain of a person;
forming first information by measuring phase-to-phase coupling between at least two electroencephalographic signals;
forming second information by measuring power of at least one electroencephalographic signal, the first and second information being related to slow waves having frequencies at or lower than 1 Hz;
performing a first comparison between the first information and corresponding coupling template information that is based on a reference brain function;

performing a second comparison between the second information and corresponding power template information that is based on a reference brain function;

combining the first and second information;

forming an index based on the combined first and second information on the basis of feature or distance calculations; and predicting a further development of neurological function level of the brain of the person towards a good outcome provided that a difference between the first information and coupling template information is smaller than a first determined threshold and at least one of the following: a power level of the second information is higher than a second determined threshold, and a difference between the second information and corresponding power template information is smaller than a third determined threshold.

18. The method of claim 17, the method further comprising normalizing the first information by performing a first comparison between the first information and corresponding coupling template information that is based on a reference brain function; and outputting information about a result of the first comparison.

19. The method of claim 17, the method further comprising normalizing the first information and the second information; and outputting information about a result of at least one of the following: the normalized first information and the normalized second information.

20. The method of claim 19, the method further comprising normalizing the second information by performing a second comparison between the normalized second information and corresponding power template information that is based on a reference brain function, and outputting information about the second comparison.

* * * * *